(12) United States Patent  
Jena et al.

(10) Patent No.: US 9,241,663 B2  
(45) Date of Patent: Jan. 26, 2016

(54) PORTABLE MEDICAL DIAGNOSTIC SYSTEMS AND METHODS USING A MOBILE DEVICE

(71) Applicant: Jana Care Inc., Newton, MA (US)

(72) Inventors: Sidhant Jena, New Delhi (IN); Michal Depa, Bangalore (IN)

(73) Assignee: Jana Care Inc., Newton, MA (US)

( * ) Notice: Subject to any disclaimer, the term of this patent is extended or adjusted under 35 U.S.C. 154(b) by 316 days.

(21) Appl. No.: 13/815,764

(22) Filed: Mar. 15, 2013

(65) Prior Publication Data

US 2014/0072189 A1    Mar. 13, 2014

Related U.S. Application Data

(60) Provisional application No. 61/849,645, filed on Sep. 5, 2012.

(51) Int. Cl.
  *A61B 5/15*   (2006.01)
  *A61B 5/00*   (2006.01)
  *A61B 5/1455* (2006.01)
  (Continued)

(52) U.S. Cl.
  CPC ......... *A61B 5/150358* (2013.01); *A61B 5/1455* (2013.01); *A61B 5/6898* (2013.01); *G01N 21/8483* (2013.01); *A61B 5/14532* (2013.01); *A61B 5/14546* (2013.01); *A61B 2560/0443* (2013.01); *A61B 2562/0295* (2013.01); *G01N 2021/8488* (2013.01)

(58) Field of Classification Search
  None
  See application file for complete search history.

(56) References Cited

U.S. PATENT DOCUMENTS 4,772,561 A * 9/1988 Genshaw ............. G01N 33/521  
422/400

5,379,214 A * 1/1995 Arbuckle ............... G01N 21/01  
128/920

(Continued)

FOREIGN PATENT DOCUMENTS

CN    102509064 A    1/2008
CN    101999881 A    4/2011

OTHER PUBLICATIONS

PCT/IB2013/002771, Search Report and Written Opinion, dated May 8, 2014, 12 pages.

(Continued)

*Primary Examiner* — Tsung-Yin Tsai
(74) *Attorney, Agent, or Firm* — Patterson Thuente Pedersen, P.A.

(57) ABSTRACT

A system and method for analysis of colorimetric test strip strips and disease management. The system can include an accessory that is operably coupled to a mobile device, the mobile device acquiring and/or analyzing images of the colorimetric test strips. The light box accessory can be detachably attached to the mobile device, or made to remain attached to the mobile device, but with the capability of having the light box accessory removed from the field of view of the camera for general photography purposes. In other embodiments, an image containing known calibration color(s) and reagent area(s) is obtained sans the light box for comparison with a previous calibration image to model changes in ambient lighting conditions and determine a color correction function. The correction can be applied to the detected reagent area color(s) for matching between the detected reagent area color(s) and reference color(s) on the reference chart. Optionally, the information can be processed and displayed to provide feedback, as well as transmitted to a health provider for analysis.

16 Claims, 22 Drawing Sheets

(51) Int. Cl.
*G01N 21/84* (2006.01)
*A61B 5/145* (2006.01)

(56) References Cited

U.S. PATENT DOCUMENTS

| | | | |
|---|---|---|---|
| 6,295,506 B1* | 9/2001 | Heinonen | A61B 5/14532 600/301 |
| 6,628,829 B1 | 9/2003 | Chasen | |
| 7,414,758 B2 | 8/2008 | Vaughn | |
| 8,145,431 B2 | 3/2012 | Kloepfer et al. | |
| 8,597,188 B2* | 12/2013 | Bernstein | A61B 5/14546 600/309 |
| 8,700,115 B2 | 4/2014 | Markle et al. | |
| 2003/0009088 A1* | 1/2003 | Korth | A61B 5/0008 600/300 |
| 2003/0113227 A1* | 6/2003 | Eyster | G01N 33/521 422/400 |
| 2005/0095697 A1 | 5/2005 | Bachur, Jr. et al. | |
| 2006/0222567 A1* | 10/2006 | Kloepfer | G01N 21/78 422/68.1 |
| 2007/0177032 A1 | 8/2007 | Wong | |
| 2008/0008370 A1 | 1/2008 | Chio | |
| 2008/0025599 A1* | 1/2008 | Cho | G01J 3/50 382/162 |
| 2010/0110439 A1* | 5/2010 | Gruler | G01N 21/255 356/440 |
| 2010/0145733 A1 | 6/2010 | Drucker et al. | |
| 2010/0254581 A1* | 10/2010 | Neeser | A61B 5/0077 382/128 |
| 2011/0038765 A1 | 2/2011 | Drucker et al. | |
| 2011/0261355 A1 | 10/2011 | Hannel et al. | |

OTHER PUBLICATIONS

Medgadget, "Dario Smartphone Powered Glucose Monitor," Medicine, Net News, Pediatrics, (available at http://www.medgadget.com), Sep. 2013, 4 pages.
Specification sheet entitled "LPV7215 580 nA Rail-to Rail Input and Output, 1.8V, Push-Pull Output Comparator," available at http://html.alldatasheet.com/html-pdf/115571/NSC/LPV7215MF/56/1/LPV7215MF.html (last visited Mar. 3, 2013).
Specification sheet entitled "Low-Power Linear Active Thermistor™ ICs," available at http://ww1.microchip.com/downloads/en/DeviceDoc/21942.pdf (last visited Mar. 3, 2013).
Mudanyali et al., "Integrated Rapid-Diagnostic-Test Reader on a Cellphone," DOI:10.1039/C2LC40235A, (Apr. 16, 2012), available at http://pubs.rsc.org, (last visited Apr. 19, 2012).
Lee, et al., "A simple and smart telemedicine device for developing regions: a pocket-sized colorimetric reader," Lab Chip, 2011, 11, 120, pp. 120-126 (Nov. 26, 2010) available at http://pubs.rsc.org, last visited May 16, 2012).
"100ppm/° C. 50 μA in SOT23-3 CMOS Voltage Reference," available at http://www.ti.com/lit/ds/symlink.ref2912.pdf (last visited Mar. 5, 2013).
Dell et al., "Towards a Point-of-Care Diagnostic System: Automated Analysis of Immunoassay Test Data on a Cell Phone", 5th ACM Workshop on Networked Systems for Developing Regions (NSDR), 2011.
Wang et al., "Integration of cell phone imaging with microchip ELISA to detect ovarian cancer HE4 biomarker in urine at the point-of-care", Lab on a Chip, 11(20), pp. 3411-3418, 2011.
J. Canny, "A Computational Approach To Edge Detection", IEEE Trans. Pattern Analysis and Machine Intelligence, 8(6), pp. 679-698, 1986.
R. O. Duda et al., "Use of the Hough Transformation to Detect Lines and Curves in Pictures". Comm. ACM, vol. 15, pp. 11-15 (Jan. 1972).
D.H. Ballard, "Generalizing the Hough Transform to Detect Arbitrary Shapes", Pattern Recognition, vol. 13, No. 2, p. 11-122, 1981.
Jung et al., "Rectangle Detection based on a Windowed Hough Transform". In Proceedings of the Computer Graphics and Image Processing, XVII Brazilian Symposium (SIBGRAPI '04), IEEE Computer Society, Washington, DC, USA, 113-120, 2004.
Szeliski, "Computer Vision: Algorithms and Applications". Springer, 2010, pp. 80-84 (Section 2.3.2).
Wakefield; BBC News Technology—TED 2013_Uchek app tests urine for medical issues; Feb. 27, 2013 (last updated at 7:09ET), 4 pages.
Aviad, Dec. 5, 2012, "Dario—Turning Your Smartphone into a Glucose Meter" (available at http://asweetlife.org/feature/dario-turning-your-smartphone-into-a-glucose-meter/), last viewed on Sep. 17, 2013.
"Piddle Simple, personal, urine analysis," (Available at http://www.linehq.com/showcase/piddle), last viewed at Sep. 17, 2013, content available prior to Mar. 15, 2013.
Darma, Medgadget, "iPhone Transformed into Microscope and Spectrometer" Oct. 4, 2011, (available at http://medgadget.com/2011/10/iphone-transformed-into-microscope-and-spectrometer.html), last viewed Sep. 20, 2013.
medgadget.com "Medgadget Cell Phone-Based Imaging Technique to Read ELISA Results" Sep. 2011, (available at http://medgadget.com/2011/09/cell-phone-based-imaging-technique-to-read-elisaresults.html), last viewed Sep. 20, 2013.
Ostrovsky, medgadget.com May 4, 2012, "iBGstar Glucometer for iPhone Now Available in U.S.", (available at http://www.medgadget.com/2012/05/ibgstar-glucometer-for-iphone-now-available-in-u-s.html, last viewed Sep. 26, 2013).
Ostrovsky, "Presentations from Health Hack Day Now available for Online Viewing (video)" May 22, 2012, (available at http://www.medgadget.com/2012/05/presentations-from-health-hack-day-now-available-for-online-viewing.html), Last viewed on Sep. 16, 2013.
Klein, "The Latest on Cellscope's Smartphone-Based Microscope and Otoscope", Jun. 21, 2012, (available at http://www.medgadget.com/2012/06/the-latest-on-cellscopes-smartphone-based-microscope-and-otoscope.html), Last viewed Sep. 16, 2013.
Dolan, "Misfit Wearables launches Shine, an elegant but rugged activity tracker" Nov. 14, 2012, (available at http://mobihealthnews.com/19066.misfit-wearables-launches-shine-an-elegant-but-rugged-activity-tracker/) last viewed Sep. 17, 2013.
CASS; "Modified iPhone Can Detect Blood Disorders", Technology Review, Oct. 5, 2011.
Ostrovsky; "iExaminer iPhone Adapter for Welch Allyn's PanOptic Ophthalmoscope Cleared in U.S. (w/video)" Jan. 2013, (Available at http://www.medgadget.com/2013/01/iexaminer-iphone-adapter-for-welch-allyns-panoptic-ophthalmoscope-cleared-in-u-s.html), last viewed Sep 17, 2013.
"Students cellphone screening device for anemis wins $250,000 prize" KurzweilAI Accelerating Intelligence News, (available at http://www.kurzweilai.net/students-cellphone-screening-device-for-anemia-wins-250000-prize), Jul. 26, 2012.
TCS3472 Color Light-To-Digital Converter with IR Filter TAOS135—Aug. 2012, Texas Advanced Optoelectronic Solutions, Inc. (TAOS).
Kerr; "Urine sample app lets users detect diseases with iPhones" Feb. 27, 2013, (available at http://news.cnet.com/8301-11386_3-57571736-76/urine-sample-app-lets-users-detect-diseases-with-iphones/); last visited Sep. 16, 2013.
Shen, et al.; "Point-of-care colorimetric detection with a smartphone" (available at www.biomicro.uc.edu_publications_Li2012LOC); Sep. 7, 2012.
"Philosys Awarded CE Mark for New Gmate ® SMART Meter An Seeks Global Telecommunications Partners", Aug. 13, 2012, New York.
"Hold the Phone for Vital Signs: Researches Turn a Smart Phone Into a Medical Monitor", Oct. 6, 2011, (available at http://www.sciencedaily.com/releases/2011/10/111006113622.htm) last viewed Sep. 16, 2014.
Gmate® Blood Glucose Monitoring System, "Philosys, Inc. Recievers FDA Approval for Gmate® VOICE Blood Glucose Meter", published Mar. 18, 2013, (available at http://www.gmate.com/announce.asp), last viewed Sep. 17, 2013.
Gmate® Blood Glucose Monitoring System, "The New iPhone 5 and Gmate® SMART Create a Dynamic Duo in Medical Diagnostics", published Sep. 25, 2012. (available at http://www.gmate.com/announce.asp), last viewed Sep. 17, 2013.

(56) References Cited

OTHER PUBLICATIONS

Gmate® Blood Glucose Monitoring System, "Philosys Awarded CE Mark for new Gmate® SMART meter and seeks global telecommunications partners", published Aug. 13, 2012, (available at http://www.gmate.com/annouce.asp), last viewed Sep. 17, 2013.

Gmate® Blood Glucose Monitoring System, "Philosys, Inc. anticipates FDA Approval for New Gmate® Blood Glucose Monitoring System", published Aug. 1, 2012, (available at http://www.gmate.com/announce.asp), last viewed Sep. 17, 2013.

* cited by examiner

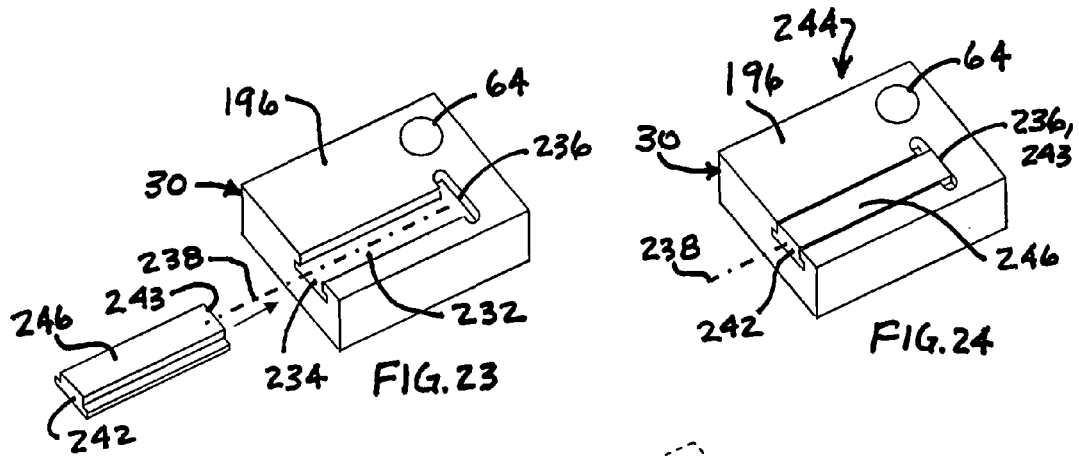
FIG. 23
FIG. 24
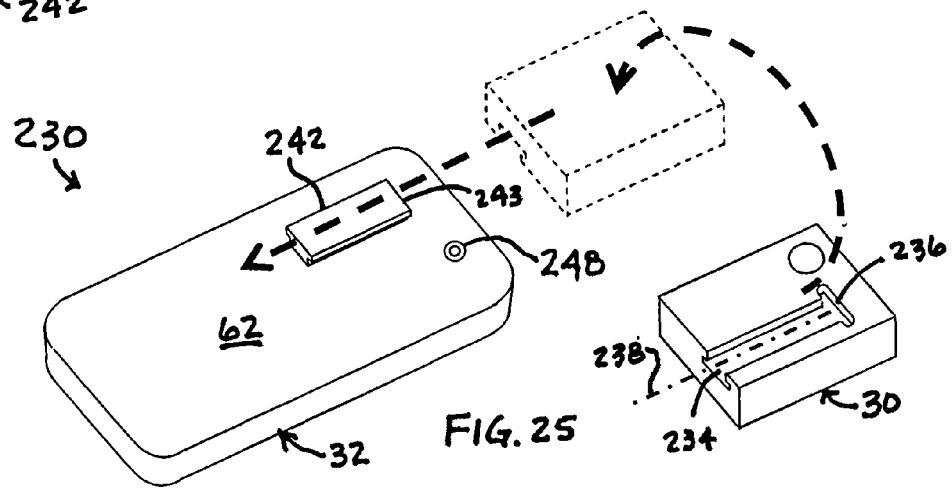
FIG. 25
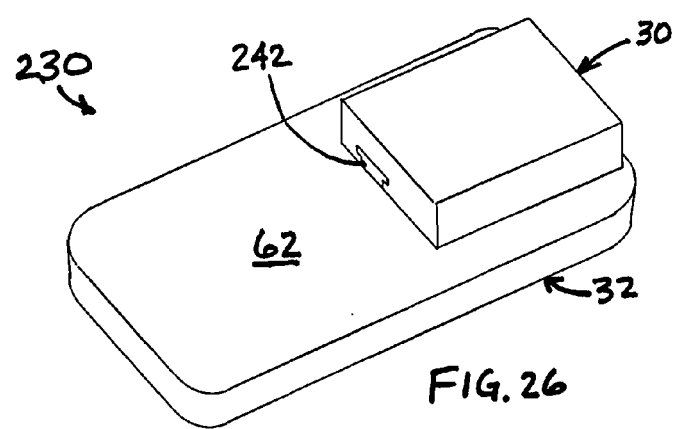
FIG. 26

PORTABLE MEDICAL DIAGNOSTIC SYSTEMS AND METHODS USING A MOBILE DEVICE

RELATED APPLICATIONS

This application claims the benefit of U.S. Provisional Patent Application No. 61/849,645, filed Sep. 5, 2012, which is hereby incorporated by reference herein in its entirety.

COMPACT DISC

A compact disc containing codes and information describing a preferred embodiment of the present invention is submitted herewith and is hereby incorporated by reference. The compact disc contains the following files and/or programs:

| TITLE | SIZE IN BYTES | DATE OF CREATION |
| --- | --- | --- |
| ColorimetricAnalysis | 10 KB | October 11, 2011 |
| colorimetricUtils | 6 KB | October 11, 2011 |
| equalize2ImagesInLab | 7 KB | October 11, 2011 |
| equalize2ImagesInRGB | 9 KB | October 11, 2011 |
| markRef5CalibBoxes | 2 KB | October 11, 2011 |
| LeaveOneOutCalib | 26 KB | February 27, 2013 |
| analyzeVideo | 20 KB | February 27, 2013 |
| detectReactionStart | 5 KB | February 27, 2013 |
| plotCompareVideos | 11 KB | February 27, 2013 |
| colorimetricAnalysis2 | 14 KB | February 27, 2013 |
| colorimetricUtils2 | 27 KB | February 27, 2013 |

FIELD OF THE INVENTION

The present invention pertains generally to devices for analysis of fluid samples, for instance medical diagnostic devices, and more particularly to analysis of colorimetric test strips using a camera, such as one provided with a smart phone or other mobile device.

BACKGROUND

Diabetes is one of the leading causes of death around the world. In India alone, there are nearly 50 million diabetic patients, a number that is expected to rise to 80 million by 2030 according to the World Health Organization.

Diabetics commonly self monitor the glucose levels in their blood several times daily. Glucose levels can be assessed using electrochemical strips that are currently prohibitively expensive for a large portion of diabetic patients worldwide. Colorimetric strips are also available but at a fraction of the cost of electrochemical strips.

Colorimetric test strips can also be used for several other blood and urine parameters, such as cholesterol, hemoglobin and ketones, as well as different applications altogether, such as testing of water quality. A modular low cost device that could perform a whole set of tests using various colorimetric strips would be an impactful innovation.

Meanwhile, the availability of mobile devices or mobile platforms have become prevalent. Examples of mobile devices include, but are not limited to, feature camera phones, smart phones, digital cameras with programming capabilities and tablets.

A low cost device that utilizes the more cost-effective colorimetric strip in a mobile platform would be a welcome addition in meeting the increasing demand for glucose monitoring and other bodily fluids.

SUMMARY OF THE INVENTION

Various embodiments of the invention provide a mobile platform for the analysis of colorimetric test strips and disease management using readings produced by this analysis. More specifically, the camera of the mobile device can be used to automatically detect the color of one or several reagent areas of the colorimetric strip. These one or several colors are compared against a set of known or standard colors previously detected from a reference and/or calibration color chart in an initial calibration and stored in the memory of the mobile device. Each of these standard colors can be associated to a specific test result reading for which the colorimetric strip is testing. These one or several detected values are then employed in a disease management platform on the mobile device. In certain embodiments, the platform records and stores these values along with additional information from the patient and transmits the values and information to a database on a remote server that a health provider can access to provide feedback for disease management. Feedback to the patient can be provided automatically by analyzing and visualizing the collected data on the mobile device, as well as by receiving personalized feedback from a health provider.

For purposes of this disclosure, a "standard color" is one having known color characteristics in a controlled or standard lighting environment, of which a "reference color" and a "calibration color" are subsets. "Reference colors" refer to standard colors that are used in manual systems for determining the closest match in a visual comparison. "Calibration colors" are standard colors used to calibrate the response of a digital camera, and can represent a range of colors particularly suited to generate accurate color correction functions. In some embodiments, a reference color or colors can also be used as a calibration color or colors.

Also for purposes of this disclosure, an "initial calibration" is a calibration performed once to gauge the response (generated color values) of a digital camera when viewing a plurality of standard colors. An "in-situ" calibration is a calibration subsequent to the initial calibration and implemented to account for changing conditions, such as ambient lighting and automatic responses implemented by the digital camera.

The detection of the color of the one or several reagent areas of the colorimetric test strip is not a trivial problem. A complication is the variety of lighting conditions the colorimetric strip can be under which affect its apparent color. Accordingly, various embodiments of the invention can perform equalization for the various lighting conditions the colorimetric test strip may be under during analysis.

Certain embodiments of the invention include a light box accessory that attaches to or is otherwise coupled with a mobile device for augmentation of digital imaging of a colorimetric strip. The light box accessory covers the mobile phone camera and restricts or eliminates light that would otherwise reach the camera of the mobile device. The lighting within the light box accessory is controlled to illuminate the light strip in a consistent manner. In one embodiment, the light box accessory aids in the alignment of the colorimetric strip with the camera of the mobile device. Furthermore, the light box accessory in various embodiments of the invention are of low profile, having a thickness (dimension along the optical axis of the camera of the mobile device) of between about 1 to 3 cm. In certain embodiments, the light box accessory can either be removed after use or rotated or flipped away for operation of the camera of the mobile device when not in use.

An aspect of the invention is that no auxiliary communication devices are required between the light box accessory and the mobile device. All communication between the light box accessory and the mobile device is done through images acquired by the digital camera of the mobile device and the conversion to color values of those images. Communication of this nature not only conveys the state of a colorimetric strip under analysis, but can also detect other conditions of the system, such as a low battery condition, a temperature out-of-range condition, and out-of-range conditions generally.

An aspect of the invention is the augmentation of a mobile device camera to provide an automatic and reliably accurate analysis of any colorimetric test strip. Colorimetric test strips, as the name implies, change color when in contact with a fluid under test. After the reaction, the final color indicates the result of the test. Colorimetric strips commonly require a visual comparison against a reference color chart to translate the resulting color to a test reading, which can lead to unreliable and inaccurate results because interpretation is based on a subjective comparison that depends on the person performing the comparison. An example of such colorimetric test strips for glucose testing are the BETACHEK Visual Strips, supplied by National Diagnostic Products Pty. Limited of Sydney, Australia.

This problem can be addressed by printing one or several calibration color patches on each colorimetric test strip. The approach is also different from including the whole reference color chart on each colorimetric test strip and finding a closest match, which, in most cases, is not feasible because the reference chart contains a large number of reference colors and colorimetric test strips have small physical dimensions.

One embodiment of the invention includes a method for equalizing the lighting conditions. The camera of the mobile device detects a set of reference colors as well as one or several calibration colors simultaneously by taking a photograph of a reference chart. All of these colors are stored as detected in the memory of the mobile device as an initial calibration. This initial calibration step need only be done once on each mobile device to take into account the specific properties of the camera of the mobile device.

To enable equalization of lighting conditions, each colorimetric strip can include, in addition to its one or several reagent areas, the same one or several calibration colors as in the reference chart previously described. The reagent area and the "in situ" calibration colors can be detected simultaneously by the camera of the mobile device. The lighting condition equalization process estimates a color correction function that models the lighting conditions using the change in the detected values of the one or several "in situ" calibration colors between the initial calibration and colorimetric test strip analysis steps. This color correction function can then be applied to the detected color values of the one or several reagent areas. The equalized reagent area colors are compared to the standard colors from the reference chart stored in memory of the mobile device to find closest matches.

In one embodiment, the comparison is performed separately for each reagent area, and once such matches are established, the test result reading of the closest reference color can be assigned to the given reagent area. Another way of obtaining a test result reading of the reagent area when it is a numerical value is to compute a weighted average of the test readings of the closest matches, or an interpolation or extrapolation of the reference color values. These results can then be used in the disease management platform on the mobile device.

In various embodiments of the invention, a colorimetric test strip analysis method comprises two phases: a lighting condition equalization phase, which can also be referred to as color correction, and a color matching phase. Color correction can entail simple white balance in digital cameras to more complex color correction in as found in advanced camera calibration algorithms.

Some embodiments of the invention image a colorimetric test strip with a mobile device camera, akin to scanning a barcode, to perform an analysis of the colorimetric strip using a software application loaded into the processor of the mobile device. The colorimetric strip can be held in front of the camera, or the utilization of a holder that holds a given colorimetric strip in front of the camera in a repeatable orientation. A color pattern can be printed on every strip to enable the software application to compensate for changing lighting conditions.

Other embodiments provide for more control of the lighting conditions. It has been found that maintaining high accuracy results across a wide range of lighting conditions can be problematic. Also, at least for embodiments where the strip is held "free hand" in front of the camera, a completely new user experience is necessary. Users are accustomed to inserting test strips into glucose meters, so the free hand technique presents a challenge of having to teach users how to properly orient the colorimetric test strip for optimal results.

Structurally, various embodiments of the invention include a light box accessory for analyzing colorimetric strips with a mobile device, the mobile device including a central processing unit and a digital camera. The accessory includes an enclosure with a proximal cover, a perimeter wall and a distal cover, the proximal cover presenting a proximal face and including structure defining a view port that passes through the proximal cover, the distal cover presenting a distal face. An aperture structure defines an aperture within the enclosure, the aperture defining a viewing axis that is concentric therewith, the viewing axis being substantially normal to the aperture and the view port of the proximal cover being substantially concentric about the viewing axis. In one embodiment, the aperture structure is integrally formed with at least one of the perimeter wall and the distal cover. In one embodiment, a structure defines a slot for insertion of a colorimetric strip, the slot being configured for orienting the colorimetric strip to intersect the viewing axis. An in situ calibration target can be disposed within the aperture structure, the in situ calibration target having predetermined color characteristics. In certain embodiments, at least one light source is disposed within the enclosure, the at least one light source being arranged for illumination of the colorimetric test strip when the colorimetric test strip is registered within the slot. The at least one light source can be a light-emitting diode.

A power source can be disposed within the enclosure and operatively coupled with the at least one light source. A switch can be operatively coupled between the power source and the at least one light source for selective activation of the at least one light source. In one embodiment, the switch is accessible on the exterior of the enclosure for manual energization of the at least one light source. The power source can comprise at least one battery. The accessory is configured to communicate with the central processing unit of the mobile device only through the digital camera of the mobile device.

The light box accessory can include a macro lens disposed within the enclosure, the macro lens being substantially concentric about the viewing axis and being located between the view port and the in situ calibration target. The light box accessory can further comprise a circuit for detection of an out-of-range condition, the circuit including a colored light source arranged to illuminate the in situ calibration target when activated. In certain embodiments, the out-of-range capabilities include a first circuit and a second circuit, each of the first and second circuits being for detection of out-ofrange conditions, each of the first and second circuits including a respective colored light source, each of the respective colored light sources being arranged to illuminate the in situ calibration target when activated. In one embodiment, the first circuit is configured to detect a first out-of-range condition and the second circuit is configured to detect a second out-of-range condition with the first out-of-range condition differs from the second out-of-range condition. A color of the respective colored light source of the first circuit can differ from a color of the respective colored light source of the second circuit.

Various embodiments of the invention comprise a method for colorimetric analysis of colorimetric test strips that implements a color correction. The method includes providing a mobile device that includes a digital camera and a central processing unit (CPU), the CPU being operatively coupled to a storage medium and configured to receive instructions from the storage medium and configuring the storage medium to include instructions readable by the CPU. In one embodiment, the instructions include:

- capturing at least one image of a plurality of standard colors with the digital camera;
- converting the at least one image of the plurality of standard colors to a plurality of initial calibration color values;
- providing a colorimetric strip exposed to a test fluid, the colorimetric strip including a reactive area;
- providing an in situ calibration target that includes at least one in situ calibration color thereon, the at least one in situ calibration color being unaffected by the presence of the test fluid, each of the at least one in situ calibration colors being substantially identical to a respective one of the plurality of standard colors;
- obtaining a digital test image that includes both an image of the reactive area of the colorimetric strip and an image of the in situ calibration target;
- analyzing portions of the digital test image known to represent the in situ calibration target to obtain a plurality of corresponding in situ quantitative color values;
- comparing the corresponding quantitative color values with the initial calibration color values;
- establishing a color correction function based on the corresponding in situ quantitative color values;
- analyzing portions of the digital test image known to represent the reactive areas of the colorimetric strip to obtain a plurality of test color values corresponding to the reactive areas; and
- applying the color correction function to the plurality of test color values; and
- converting the plurality of test color values to at least one test reading.

In one embodiment, the plurality of standard colors are reference colors. The at least one image of a plurality of standard colors can include both calibration colors and reference colors. The method can further comprise linearizing the initial calibration color values and the in situ quantitative color values. In one embodiment, the method comprises storing the plurality of initial calibration color values to the storage medium, and/or recalling the plurality of initial calibration color values from the storage medium before the comparing step.

BRIEF DESCRIPTION OF THE DRAWINGS

FIGS. 23 through 26 are perspective views of a rail mounting system for mounting a light box accessory to a mobile device in an embodiment of the invention;

DETAILED DESCRIPTION OF EMBODIMENTS OF THE INVENTION

Figure 1:
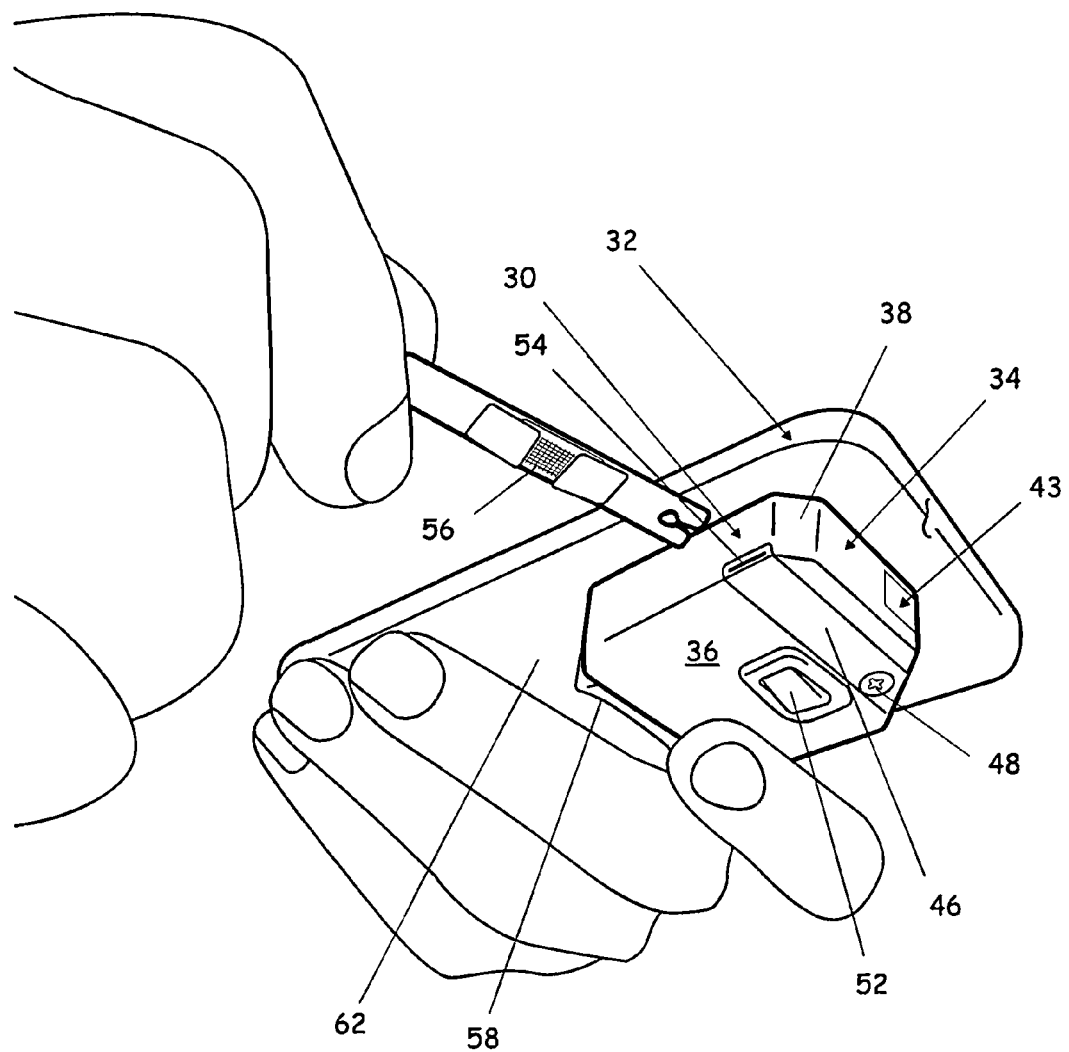
FIG. 1 is a perspective view of a light box accessory operably attached to a mobile device in an embodiment of the invention.
Figure 2:
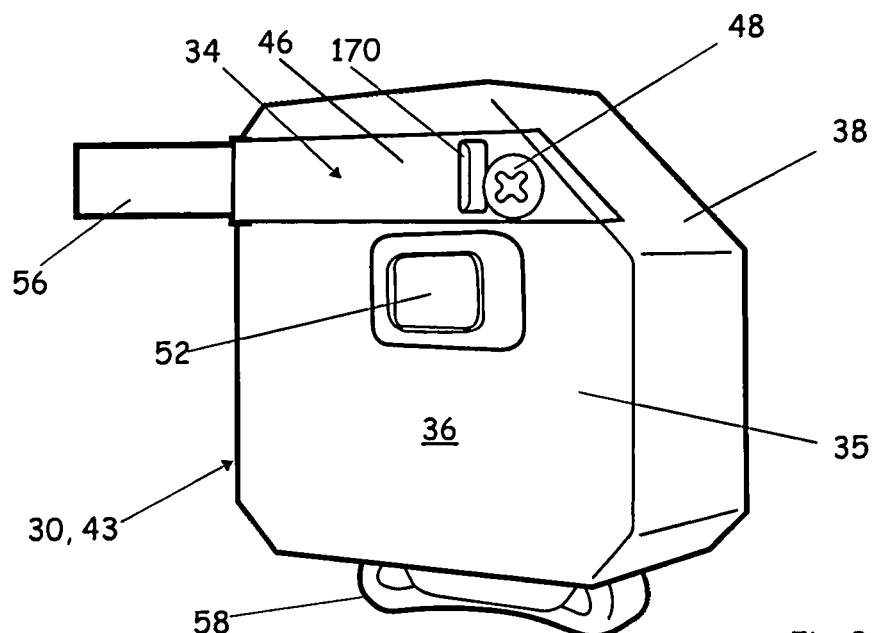
FIG. 2 is a perspective view the light box accessory of FIG. 1.
Figure 3:
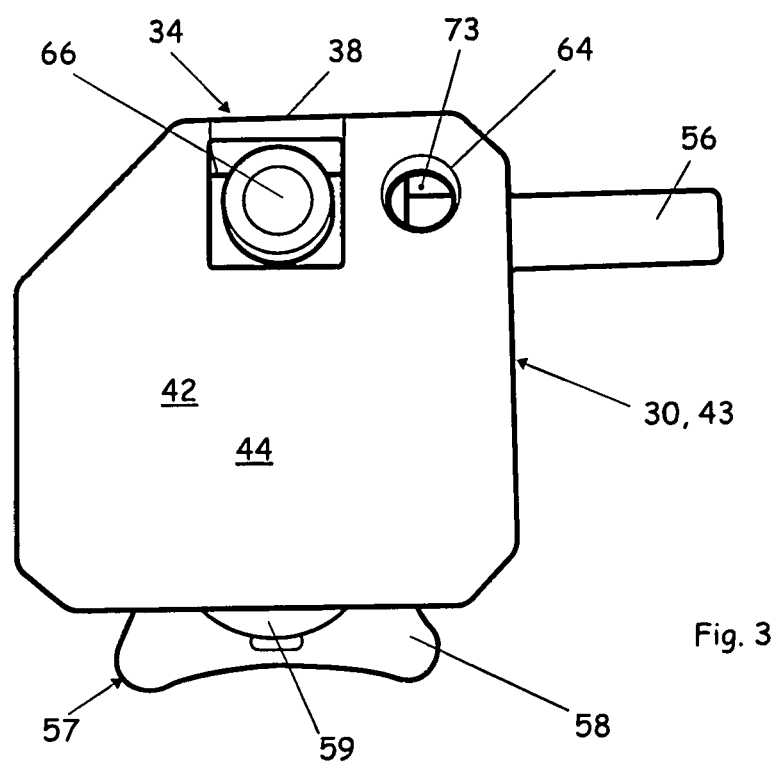
FIG. 3 is a perspective view of a proximal face of the light box accessory of FIG. 1 in an embodiment of the invention.

Referring to FIGS. 1 through 3, a light box attachment or accessory 30 adapted for coupling with a mobile device 32 is depicted in an embodiment of the invention. In one embodiment, the light box accessory 30 includes a housing 34 having a distal cover 35 that presents a distal face 36 and a perimeter wall 38 that cooperates with a proximal cover 42 to define an enclosure 43, the proximal cover 42 having a proximal face 44. In one embodiment, the distal face 36 and perimeter wall 38 accommodates a test strip adaptor 46 that is secured to the housing 34 with a fastener 48. The distal face 36 can also include a power switch 52 accessible by the user for manual energization of a light source within the housing 34. The test strip adaptor 46 and perimeter wall 38 can cooperate to define a slot 54 for insertion of a colorimetric test strip 56.

In one embodiment, the light box accessory 30 includes an on-board power source 57. In the depicted embodiment, the power source 57 includes a battery holder 58 that accommodates button- or coin-type batteries 59 and is inserted into a slot (not visible in the FIGS.) in the perimeter wall 38. It is understood that other on-board power sources and battery arrangements can be utilized.

The proximal cover 42 is adapted to contact a back face or camera face 62 of the mobile device 32. The proximal cover 42 can comprise a compliant gasket material. The proximal cover 42 also defines a view port 64 that is aligned with and opposing the test strip adaptor 46 and positioned to align with the camera lens of the mobile device 32, thus enabling viewing of the colorimetric test strip 56 therethrough. In one embodiment, a magnet 66 is secured within the housing 34, an exposed face 68 of the magnet 66 being accessible from the proximal face 44 of the housing 34.

For purposes of this disclosure, "distal face," "distal surface" or "distal side" refers to a surface, face or side of the housing 34 that faces generally away from the mobile device 32 when the light box accessory 30 is in operation. "Proximal face," "proximal surface" or "proximal side" refers to a face, surface or side of the housing 34 that faces generally towards the mobile device 32 when the light box accessory 30 is in operation. Also, "mobile device" is any mobile computing device having digital imaging capability that can be programmed to acquire and/or process information from a digital image. Examples of mobile devices include, but are not limited to, feature camera phones, smart phones, digital cameras with programming capabilities and tablets.

Figure 4:
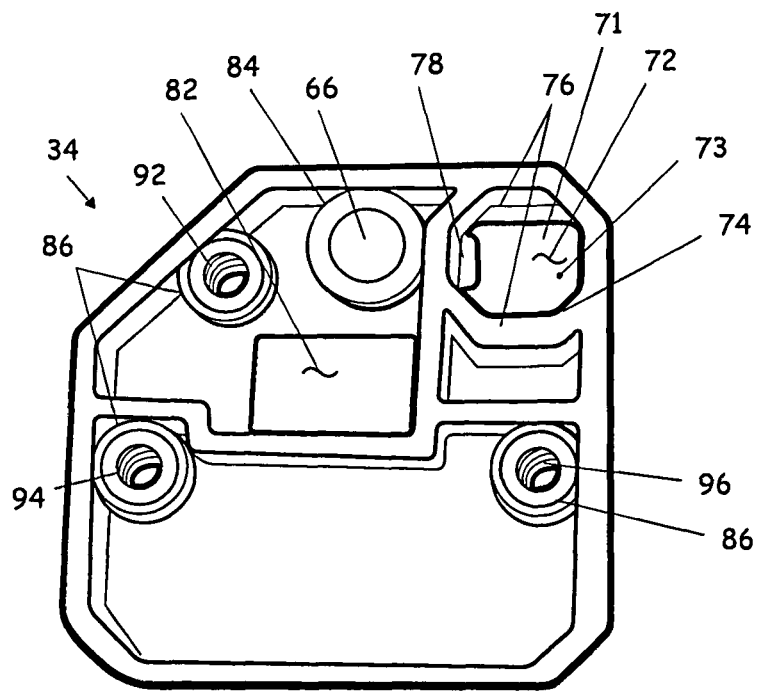
FIG. 4 is a perspective view of the housing of the light box accessory of FIG. 1 from the proximal side.
Figure 5:
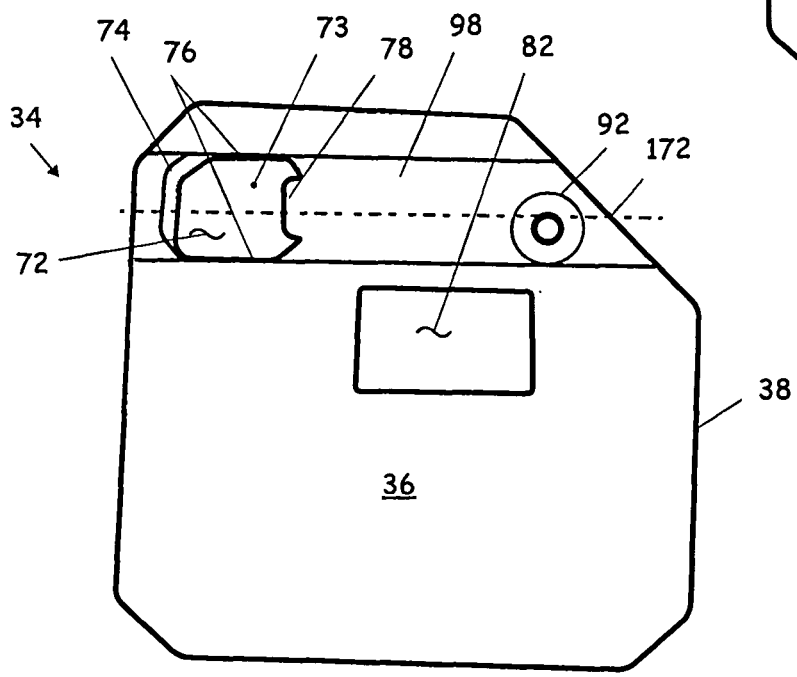
FIG. 5 is a perspective view of the housing of the light box accessory of FIG. 1 from the distal side.

Referring to FIGS. 4 and 5, the housing 34 is depicted with the proximal cover 42 removed. In the depicted embodiment, the housing 34 includes an aperture structure 71 that defines an aperture 72 within the enclosure 43, the aperture 72 defining a viewing axis 73. In one embodiment, the aperture structure 71 includes a proud structure 74 about the perimeter of the aperture 72. In one embodiment, the aperture 72 is cropped on opposing sides by ledges 76 that are formed on the distal face 36 of the housing 34. The proud structure 74 can also include a tab 78 that extends radially inward therefrom. The housing 34 also defines an opening 82 for mounting of the power switch 52, a receptacle 84 for mounting the magnet 66, and receptacles 86 for mounting threaded female inserts 92, 94 and 96. In one embodiment, a mounting channel 98 is provided on the distal face 36 of the housing 34 to accommodate the test strip adaptor 46. While the depicted embodiment portrays the aperture 72 as polygonal, other geometries can also be defined, such as a circular, oval or elliptical geometry.

Figure 6:
FIG. 6 is a plan view of an "in situ" calibration target in an embodiment of the invention.
Figure 7:
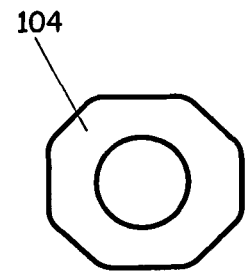
FIG. 7 is a plan view of a diffuser insert in an embodiment of the invention.

Referring to FIGS. 6 and 7, an "in situ" calibration target 102 and a diffuser insert 104 are depicted in embodiments of the invention. The in situ calibration target 102 is configured to fit within the aperture 72 in contact with the proximal faces of the ledges 76 and the proximal face of the tab 78. The in situ calibration target 102 is also configured to cover only a portion of the aperture 72. The diffuser insert 104 is configured to fit within the aperture 72. In one embodiment, the in situ calibration target 102 is disposed between the diffuser insert 104 and the proximal faces of the ledges 76 and tab 78. In one embodiment, a macro lens (not depicted) is also disposed in the aperture 72 of the housing 34, the optical axis of the lens being concentric with a central axis of the aperture 72.

Figure 8:
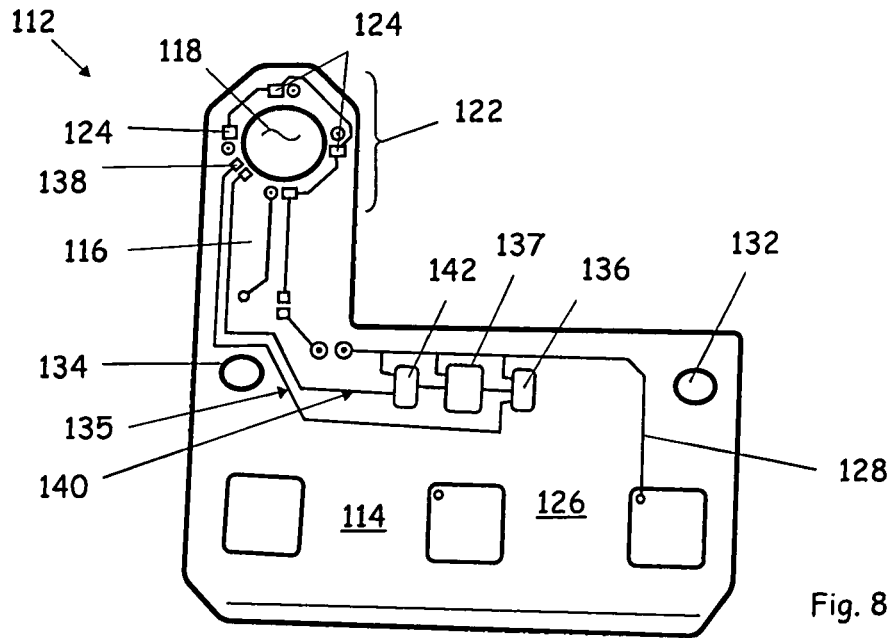
FIG. 8 is a plan view of the proximal face of a circuit board in an embodiment of the invention.

Referring to FIG. 8, a circuit board 112 is presented in an embodiment of the invention. The circuit board 112 includes a base portion 114 and an extended portion 116 that extends from the base portion 114. An aperture 118 is located at a free end portion 122 of the extended portion 116. In one embodiment, a plurality of light-emitting diodes (LEDs) 124 are disposed on a distal face 126 of the circuit board 112 proximate the aperture 118, the LEDs 124 being operatively coupled to a circuit 128 for selective activation. The circuit board 112 also includes mounting holes 132 and 134 for coupling with threaded female inserts 94 and 96, respectively, in the housing 32. The circuit board 112 is so shaped to enable clearance for the power switch 52 and access to the magnet 66 when the circuit board 112 is mounted in the housing 34.

It is noted that while the depicted embodiment portrays a plurality of LEDs, utilization of a single LED is also contemplated. Also, other light sources besides LEDs and available to the artisan and amenable to incorporation into the handheld system depicted herein can be utilized.

An alternative embodiment may eliminate the power switch 52. Instead, the plurality of LEDs 124 can be activated by a switch that is internal to the light box accessory 30 and senses the presence of the colorimetric strip 56 (for example, by a roller lever arm toggle micro switch or an optical path detection switch). Such an arrangement can provide the advantage of assuring that the colorimetric strip 56 is properly loaded into the light box accessory 30 before analysis images can be acquired. The arrangement can also prevent inadvertent activation of the LEDs that could drain the batteries.

In certain embodiments, the light box accessory 30 includes circuits for detection of an out-of-range condition or conditions, examples of which are described below.

Figure 8A:
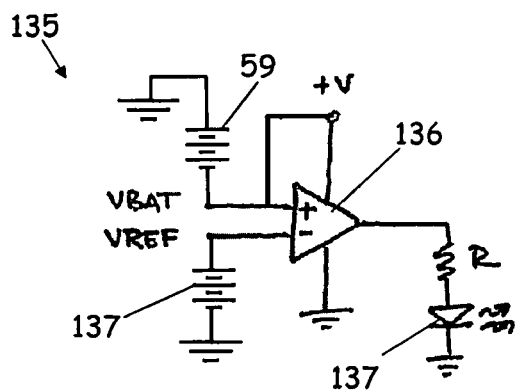
FIG. 8A is a schematic of a low battery detection circuit in an embodiment of the invention.

Referring to FIG. 8A and again to FIG. 8, a low battery detection circuit 135 is depicted in an embodiment of the invention. The low battery detection circuit 135 can include a comparator 136 operatively coupled to a reference voltage source 137 and a colored light source 138, such as a colored LED. A non-limiting example of a voltage source 137 is the REF29xx CMOS voltage reference, manufactured by Texas Instruments, Inc. of Dallas, Tex., USA, the specifications of which is entitled "100 ppm/° C., 50 µA in SOT23-3 CMOS Voltage Reference," available at http://www.ti.com/lit/ds/symlink/ref2912.pdf (last visited Mar. 5, 2013).

The colored light source 138 can pass light primarily across a narrow band pass correlating roughly to a color (e.g., red, green, amber) and is arranged to illuminate the in situ calibration target 102 upon activation. An non-limiting example of a comparator 136 suitable for use in the low battery detection circuit 135 is the National Semiconductor LPV7215MF, the specification sheet for which is entitled "LPV7215 580 nA Rail-to-Rail Input and Output, 1.8V, Push-Pull Output Comparator," available at http://html.all-datasheet.com/html-pdf/115571/NSC/LPV7215MF/56/1/LPV7215MF.html (last visited Mar. 3, 2013).

In operation, the comparator 136 compares a voltage Vbat of the power source 59 (straight or divided down) against a reference voltage Vref of the reference voltage source 137. When the Vbat drops below the Vref, the comparator 136 energizes the colored light source 138.

Figure 8B:
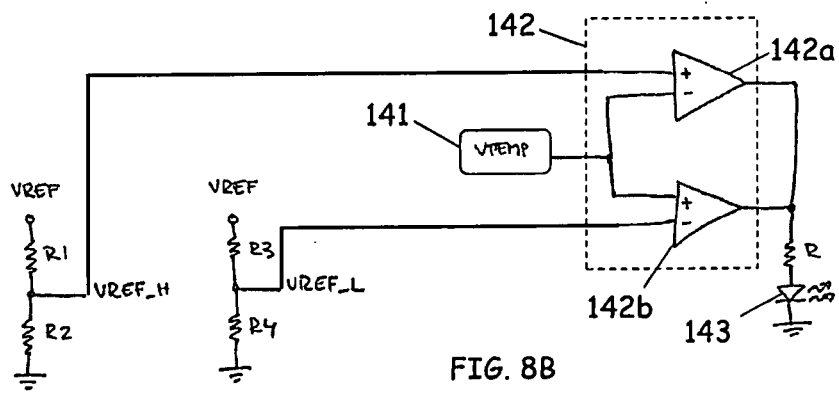
FIG. 8B is a schematic of a temperature out-of-range detection circuit in an embodiment of the invention.

Referring to FIG. 8B and again to FIG. 8, a temperature out-of-range detection circuit 140 is depicted in an embodiment of the invention. The temperature out-of-range detection circuit 140 can include a temperature sensor 141, a dual comparator 142 and a colored light source 143. The temperature sensor 141 can output a voltage Vtemp according to a known correlation with temperature of the sensor 141. The colored light source 143, such as a colored LED, can pass light primarily across a narrow band pass correlating roughly to a color (e.g., red, green, amber) and is arranged to illuminate the in situ calibration target 102 upon activation. The Vref_h and Vref_L voltages can be generated, for example, by dividing a voltage reference Vref using resistors, depicted as resistors R1, R2, R3 and R4 in FIG. 8B. In one embodiment, Vref can be sourced from the voltage source 137.

An non-limiting example for the dual comparator 142 suitable for use in the temperature out-of-range circuit 140 is the MCP9700/9700A or /9701A, manufactured by Microchip Technology, Inc. of Chandler AX, the specification sheet for which is entitled "Low-Power Linear Active Thermistor™ ICs," available at http://ww1.microchip.com/downloads/en/DeviceDoc/21942e.pdf (last visited Mar. 3, 2013).

As depicted in FIG. 8, a plurality of the out-of-range circuits (e.g., circuits 135 and 140) can be implemented in the same light box accessory 30. The colors emitted by the light sources (e.g., light sources 138 and 143) can pass light at different band passes, which can be useful when each circuit is designed to detect a different parameter or different out-of-range thresholds.

The dual comparator 142 can include a first comparator 142a and a second comparator 142b. The first comparator 142a compares the voltage Vtemp output from the temperature sensor 141 against a high reference voltage Vref_h and activates the colored light source 143 when Vref_h exceeds a predetermined voltage that corresponds to a predetermined high temperature for the output of the temperature sensor 141. The second comparator 142b compares the voltage Vtemp output from the temperature sensor 141 against a low reference voltage Vref_l and activates the colored light source 143 when Vref_l drops below a predetermined voltage that corresponds to a predetermined low temperature for the output of the temperature sensor 141.

Functionally, and as explained in greater detail below in relation to FIG. 37, illuminating the in situ calibration target 102 can provide a mechanism for communicating to the mobile device 32 that an out-of-range condition has occurred. Consider, for example, an illumination of the in situ calibration target 102 by the colored light source 138 of the low battery detection circuit 135, and where the colored light source 138 is configured to illuminate the in situ calibration target 102 with, again by example, a substantially amber-colored light. The presence of the amber-colored light overlaid on the broadband illumination provided by the plurality of LEDs 124, will cause an increase in the intensity (absolute or normalized) of certain portions of the color spectrum relative to the intensities observed when illuminated by the plurality of LEDs 124 alone. Furthermore, the colors affected by the illumination from colored light source 138 can be known a priori by calibration of the in situ calibration target 102 under illumination from the light source 138. Non-limiting examples of devices utilized for the colored light source 138 and their attendant spectra include: an amber LED (operating with peak intensity in the 600-625 nm band pass); a green LED (operating with peak intensity in the 500-575 nm band pass); a red LED (operating with peak intensity in the 630-650 nm band pass); and a blue LED (operating with peak intensity in the 460-480 nm band pass).

Accordingly, when the colors of the image are analyzed by the mobile device 32, the mobile device 32 can be configured to interpret the increase of the intensities of these known colors as an indication that there the low battery circuit 135 has detected a low battery condition.

The same general procedure can be implemented using other colored light sources to detect other out-of-range conditions. For example, the light source 143 for the temperature out-of-range detection circuit 140 can be configured to illuminate the in situ calibration target 102 with a different color (e.g., red) than the light source 138 of the low battery detection circuit 135 (e.g., amber). Illuminating the in situ calibration target 102 with the different colored (red) light causes different a different color profile to be observed than for either the broadband illumination provided by the plurality of LEDs 124 alone, or the broadband illumination plus the colored light (e.g., amber) from the plurality of LEDs 124 and the colored light source 138. Thus, the mobile device 32 can distinguish which of the plurality out-of-range conditions (e.g., low battery or temperature) are being communicated by the light box accessory 30.

In various embodiments of the invention, all such "communication" is via the camera of the mobile device 32. No additional lanes of communication (e.g., USB, wireless encryption) are needed. In this way, communication from the light box accessory 30 to the mobile device 32 is performed with analog devices.

Figure 9:
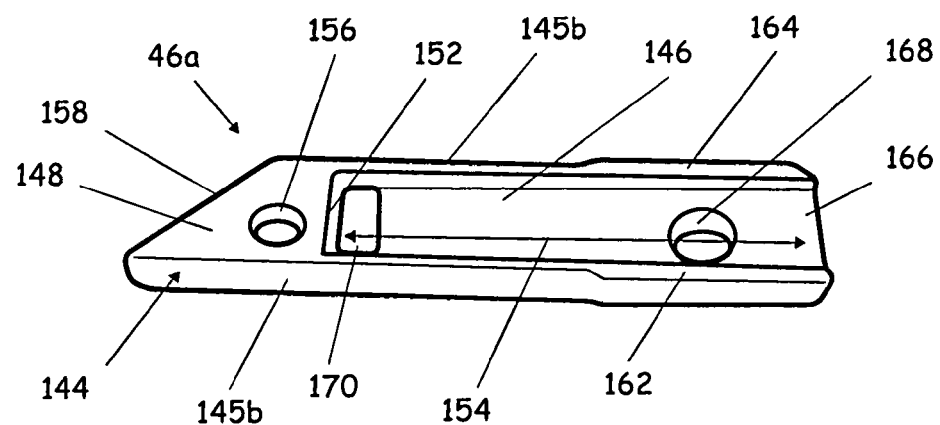
FIGS. 9 and 10 are perspective views of test strip adaptors in embodiments of the invention.
Figure 10:
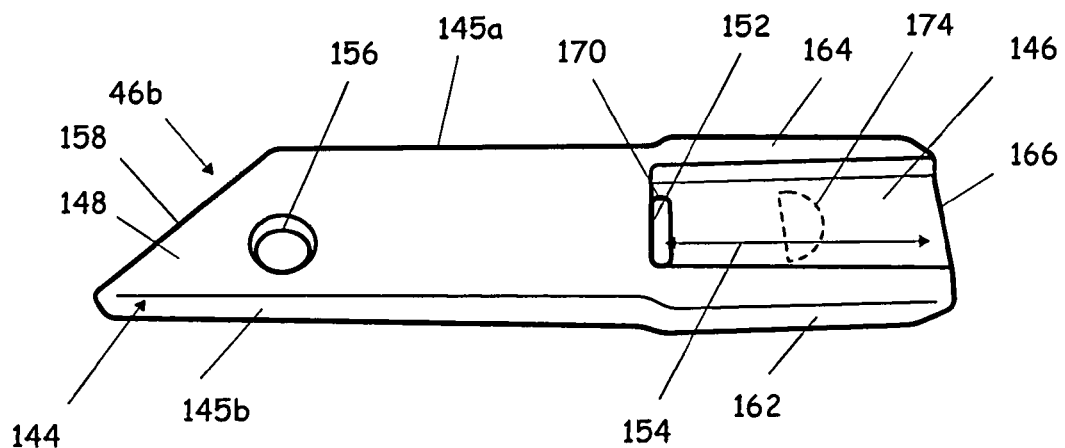

Referring to FIGS. 9 and 10, test strip adaptors 46a and 46b (referred to generically and collectively as test strip adaptor(s) 46) that define and are accessible from the slot 54 are presented in embodiments of the invention. Each test strip adaptor 46 comprises a bar 144 having two parallel sides 145a and 145b and a recess 146 formed on a proximal face 148. The recess 146 extends along a first portion of the length of the bar 144, terminating at an abutting end 152 and defining an insertion length 154 for the colorimetric test strip 56. A mounting hole 156 is disposed proximate a first end 158 of the bar 144. The parallel sides 145a and 145b of the bar 144 include rails 162 and 164 that extend along a portion of the bar 144 and near a second end 166 of the bar 144, the second end 166 being opposite the first end 158 of the bar. In one embodiment, an access hole 168 is provided that passes through the bar 144. In one embodiment, a through-slot 170 is included proximate the abutting end 152 of the recess 146 for visual verification that the colorimetric strip 56 is fully inserted.

Assembly of the depicted embodiment includes pressing or otherwise securing the magnet 66 and threaded female inserts 92, 94 and 96 into the respective receptacles 84 and 86 of the housing 34. The in situ calibration target 102 is disposed within the aperture 72 from the proximal side, the in situ calibration target 102 contacting the ledges 76 and covering a portion of the opening defined by the aperture 72. The diffuser insert 104 is then disposed in the aperture 72, registering against the proximal face of the in situ calibration target 102 and the tab 78. For embodiments implementing a macro lens, the macro lens can be mounted on the aperture 118 of the circuit board 112 and held in place by the proximal cover 42.

The circuit board 112 is then mounted to the housing 34 so that the aperture 118 on the free end portion 122 of the extended portion 116 is in substantial alignment with the aperture 72 of the housing 34 and fastened to the threaded female inserts 94 and 96 via the mounting holes 132 and 134. In this orientation, the free end portion 122 of the extended portion 116 captures the diffuser insert 104 and the in situ calibration target 102 within the aperture 72, and the LEDs 124 are in contact with or nearly in contact with the diffuser insert 104.

The test strip adaptor 46 is secured to the distal face 36 of the housing 34 by inserting the test strip adaptor 46 into the mounting channel 98 and securing it in place with the fastener 48 that is coupled with the threaded female insert 92 via the mounting hole 156 on the test strip adaptor 46. In one embodiment, the test strip adaptor 46 is inserted laterally into the mounting channel 98 along a channel axis 172 (FIG. 5), with the rails 162 and 164 slidingly engaging grooves formed along the edges of the mounting channel 98 (grooves not visible in the FIGS.).

Functionally, the test strip adaptor 46a is suitable for use with "two sided" strips (e.g. strip 190, discussed below attendant to FIG. 13), where the sample is placed on the strip after being mounted to the light box accessory 30. Application of the sample is accomplished via the access hole 168. Test strip adaptor 46b is suitable for use with "one sided" strips, where the sample is applied to the strip prior to being mounted within the light box accessory 30.

the view port 64, aperture 118 of the circuit board 112 and aperture 72 of the housing 34 are substantially aligned so that the camera of the mobile device 32 can view a target zone 174 within the recess 146 of the test strip adaptor 46. For embodiments utilizing the in situ calibration target 102, the target zone 174 defined on the test strip adaptor 46 is clipped, as depicted in FIG. 10. The proud structure 74 of the aperture 72 can define a barrier that, along with the proximal cover 42 and the test strip adaptor 46, significantly blocks ambient light from illuminating the target zone 174 of the test strip adaptor 46.

The diffuser insert 104 acts to diffuse the light emitted by the LEDs 124 to provide substantially uniform lighting of the in situ calibration target 102 and target zone 174. The in situ calibration target 102 can be of a known color, color scheme or combination of colors suitable for calibration of the camera of the mobile device 32, as explained attendant the discussion of FIGS. 21-26 below.

Figure 11:
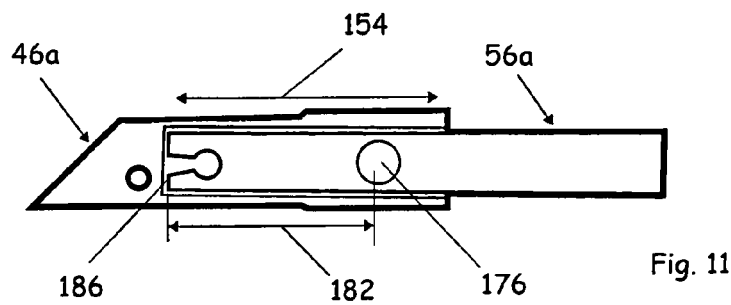
FIGS. 11 and 12 are perspective views of test strip adaptors with colorimetric strips mounted thereto in embodiments of the invention.
Figure 12:
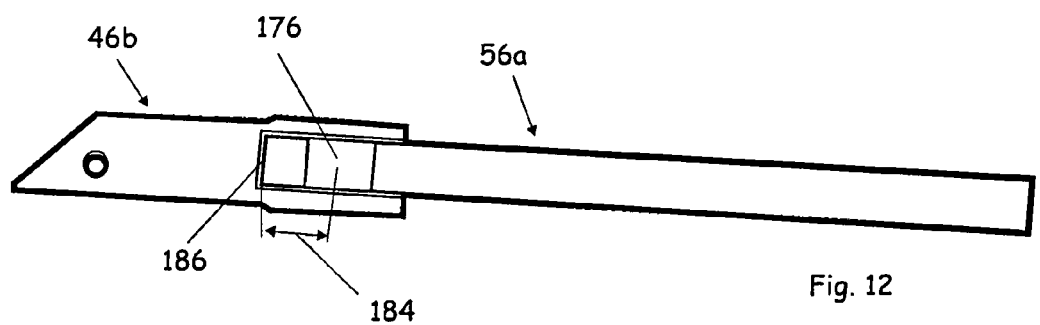

Referring to FIGS. 11 and 12, colorimetric test strips 56a and 56b (referred to generically as the colorimetric test strip 56) are presented that are mounted in the strip adaptors 46a and 46b, respectively. Functionally, the insertion length 154 defined by the recess 146 on the test strip adaptor 46 is tailored to align a reactive zone 176 of the colorimetric test strip 56 with the target zone 174 of the test strip adaptor 46. For example, the test strip adaptor 46a is designed to align a BETACHEK G5 test strip, whereas the test strip adaptor 46b is designed to align a BETACHEK Visual test strip. The reactive zones 176 of the G5 and Visual test strips are centered at different distances 182 and 184 from an insertion end 186 of the respective test strip. The abutting end of the respective recesses 146 are located so that the reactive zone 176 of the respective colorimetric test strip 56a or 56b is aligned over the target zone 174 of the respective test strip adaptor 46a or 46b when the colorimetric test strip 56 is inserted and registered against the abutting end 152. The width of the recess 146 can also be dimensioned to provide a desired fit with the colorimetric test strip 56.

In operation, the camera of the mobile device 32 is aligned over the view port 64 of the proximal cover 42 to view the in situ calibration target 102 and target zone 174 inside the light box accessory 30. In one embodiment, a magnet (not depicted) is mounted on the camera face 62 of the mobile device 32. The exposed face of the magnet on the mobile device 32 is oriented to have complementary polarity with the exposed contact face 68 of the magnet 66 on the light box accessory 30. The attraction between the magnets detachably secures the proximal face 44 of the light box accessory 30 against the camera face 62 of the mobile device 32. Also, the magnet on the mobile device 32 is positioned to align with the magnet 66 on the light box accessory 30 when the lens of the camera is aligned with the view port 64.

The colorimetric strip 56 is inserted into the recess 146 of the test strip adaptor 46 along the channel axis 172 until the insertion end 186 contacts the abutting end 152 of the recess 146. The power switch 52 is activated to provide energy to the LEDs 124, which floods the aperture 72 with light via the diffuser insert 104 to illuminate the colorimetric test strip 56. The mobile device 32 is then operated to execute the application software in acquiring and evaluating images of the colorimetric test strip 56.

Figure 13:
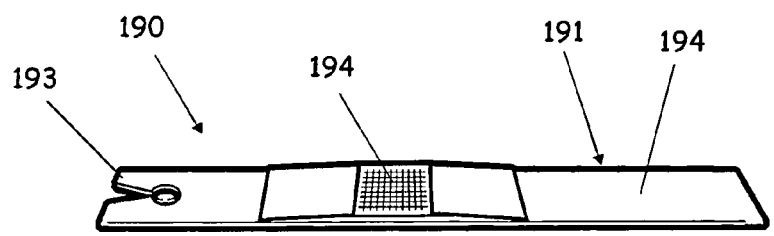
FIGS. 13 and 14 are perspective views of a proximal face and a distal face, respectively, of a colorimetric test strip in an embodiment of the invention.
Figure 14:
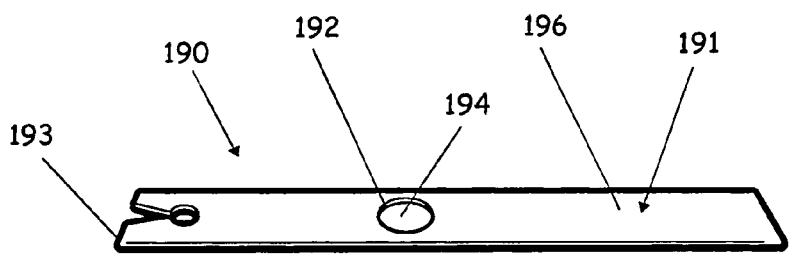

Referring to FIGS. 13 and 14, a colorimetric test strip 190 is depicted for use with the test strip adaptor 46a in an embodiment of the invention. The colorimetric test strip 190 includes a substrate 191 having a through hole 192 that is located substantially in the same location relative to an insertion end 193 as the reactive zone 176 of other standard test strips (e.g., the BETACHEK G5 test strip). Materials for a reactive zone 194 are disposed on a proximal face 196 of the of the colorimetric test strip 190 over the through hole 192, and are accessible from a distal face 198 of the colorimetric test strip 190 through the through hole 192. When the colorimetric test strip 190 is fully inserted in the test strip adaptor 46a, the through hole 192 is in alignment with the access hole 168 on the test strip adaptor 46a and is accessible from the distal face 196. The alignment between the access hole 168 and the through hole 192 enables depositing the fluid under test onto the colorimetric test strip 190 after insertion into the light box accessory 30.

The colorimetric strip of FIGS. 13 and 14 are representative of a two-sided strip wherein the fluid (e.g., blood droplet) is applied to one side and the reactive change observed on the other. When two-sided strips are utilized, the software application controlling the mobile device 32 can be programmed to observe the onset of the color change in a video or time-lapsed fashion and to acquire a digital image of the reactive segment of the two-sided strip at a predetermined time interval after the onset. The digital image acquired at the predetermined time interval can then be analyzed to provide the test results. The predetermined time can be established at a time period known to provide repeatable results, thereby enhancing the accuracy and reliability of the measurement.

Figure 15:
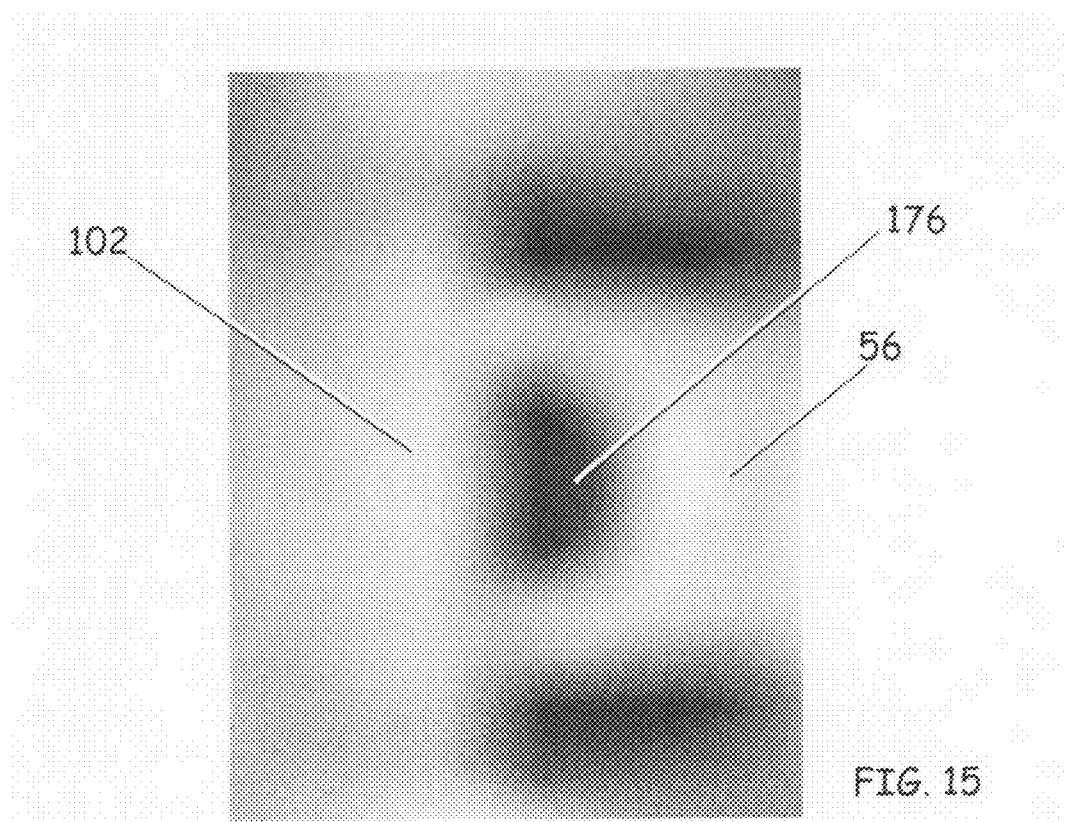
FIG. 15 is an image captured by a mobile device viewing a colorimetric strip and an "in situ" calibration target in the light box accessory of FIG. 1.
Figure 16:
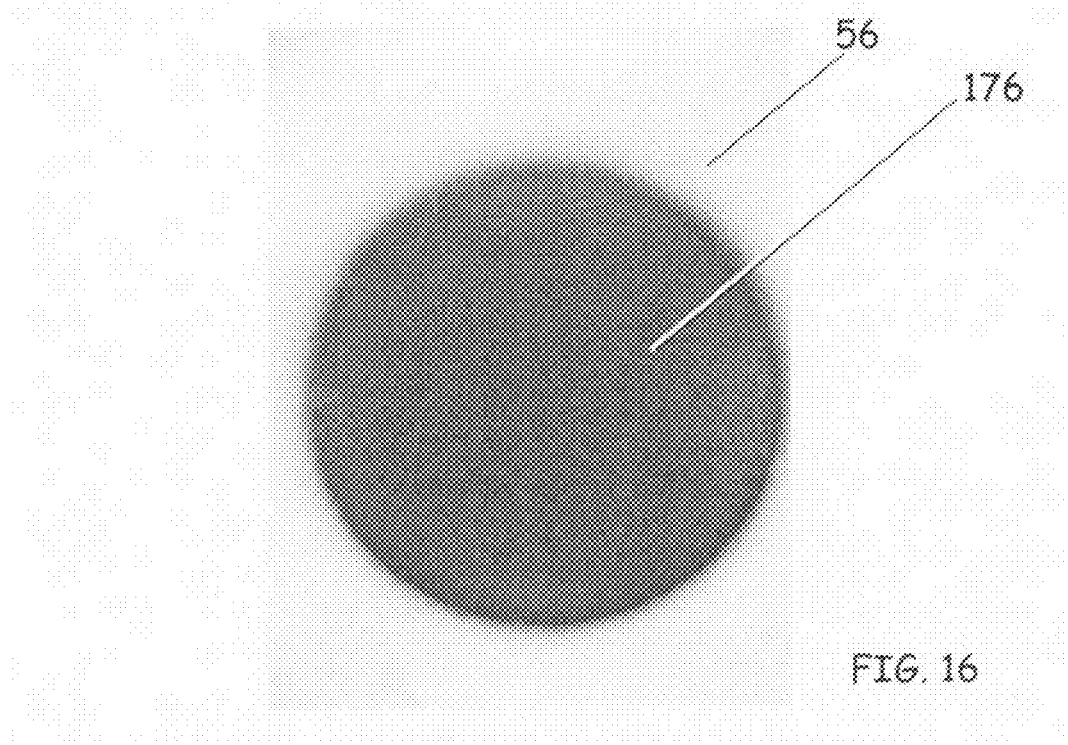
FIG. 16 is an image captured by a mobile device viewing a colorimetric strip using a macro lens in an embodiment of the invention.

Referring to FIGS. 15 and 16, images of the colorimetric test strip 56 in position over the target area 174 as captured by the camera of the mobile device 32 are presented in embodiments of the invention. The image of FIG. 15 includes both the in situ calibration target 102 and the reactive zone 176, which are blurry because the focusing system of the camera of the mobile device 32 is not designed to capture images that are only a few millimeters away. For some software applications that can be loaded into the mobile device 32, such an image is sufficient for analysis because the detected color values at certain pixels of the image are unaffected by the blurred image.

For the image of FIG. 16, a macro lens was disposed between the camera of the mobile device 32 and the reactive zone 176 of the colorimetric strip 56, with the in situ calibration target 102 removed. The image is not as blurry. The macro lens can be characterized as having an example and non-limiting focal length on the order of 1 to 10 mm. For the image of FIG. 16, for example, it was found that a focal length of approximately 6 mm enabled the camera to capture the image while focused at infinity. Generally, the focal length of the macro lens need not be closely specified because of the autofocus capabilities of existing mobile device cameras.

While the light box accessory 30 provides a controlled light environment, some image normalization may still be necessary. Some of the parameters of the camera, such as the exposure time, are automatically selected by the hardware of the camera of the digital imaging device and cannot be compared to initial calibration images stored in memory to produce a reading value. Also, different phone models have different camera parameters and characteristics. Thus, normalization of the image using the in situ calibration target 102, while not always necessary, is often beneficial to avoid having to perform a calibration for each mobile device model. In the depictions herein, the in situ calibration target 102 is of a solid white color, but other colors as well as a more complex color pattern can be utilized. In one embodiment, the in situ calibration target 102 includes patches of different colors, for example, a yellow stripe, a green-yellow stripe and a green stripe. In another embodiment, the in situ calibration target 102 includes a patch or patches of reference colors.

In one embodiment, alignment of the light box accessory 30 with the camera of the mobile device 32 is facilitated using a pattern (not depicted) within the light box accessory 30 that is seen by the camera when the light box accessory 30 is attached. The pattern can be printed on the target zone 174 of the test strip adaptor 46, on the in situ calibration target 102, or can be included on a separate strip that is inserted into the test strip adaptor 46. In one embodiment, the image of the pattern could be presented on the display of the mobile device 32, along with a desired position of the same pattern. The user would then simply align the imaged and the preferred patterns to align the camera. In another embodiment, the pattern can be designed so that the software application determines what direction the attachment needs to be translated for adequate alignment, and posts instructions as to which direction to translate the light box accessory 30 in order to achieve the alignment. For example, a right arrow on the display would indicate to the user to translate the light box accessory 30 to the right, and so on.

In certain embodiments, appurtenances are provided to key the coupling of the light box accessory 30 to the mobile device 32 so that, after an initial alignment, subsequent mounting of the light box accessory 30 results in an aligned orientation. For example, the receptacle 84 of the magnet 66 could have an outer perimeter that is polygonal (not depicted), and the magnet that mounts to the mobile device 32 could be disposed in a frame (not depicted) that surrounds the phone magnet and is also mounted to the camera face 62, the frame being configured to mate with the polygonal outer perimeter of the receptacle 84. The alignment procedure would then be executed to establish the proper location of the phone magnet before affixing the phone magnet to the mobile device 32. In one embodiment, alignment of the light box accessory 30 can be accomplished with protrusions (not depicted) that contact the perimeter wall 38 of the light box accessory 30. The protrusions can be mounted to the mobile device during or immediately after an initial alignment process to triangulate the orientation of the light box accessory 30 for subsequent mountings.

In one embodiment, digitally readable information (e.g., 2D or 3D bar codes) is printed on a strip inserted into the light box accessory. The information can be utilized in at least two ways: (1) to "authenticate" the strip being used, thus ensuring that only authorized strips are being utilized by the system, and (2) to read calibration information for use by the mobile device in analyzing images of the test strip. The calibration information can comprise calibration coefficients that are then loaded into a general curve form, or can provide instructions (e.g., an internet address) to accessing the information. The information can be printed on the colorimetric strip itself, or be printed on a separate strip that accompanies a package of colorimetric strips.

Figure 17:
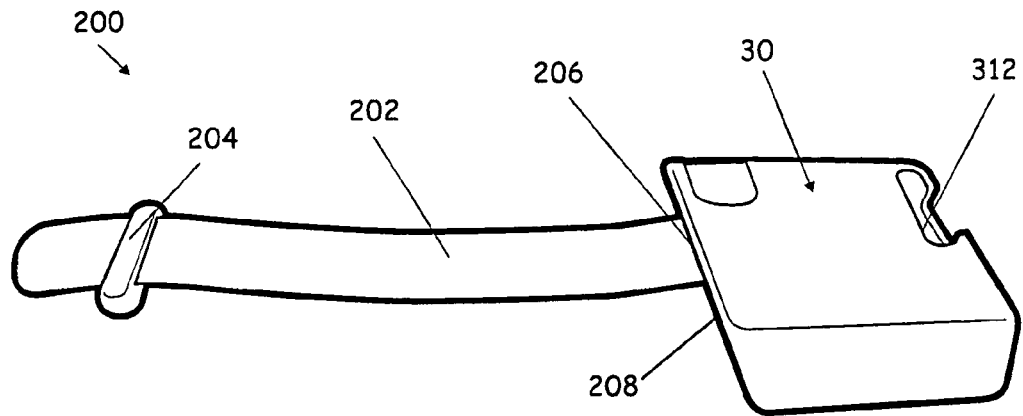
FIGS. 17 and 18 are perspective views of an elastic strap for mounting a light box accessory to a mobile device in an embodiment of the invention.
Figure 18:
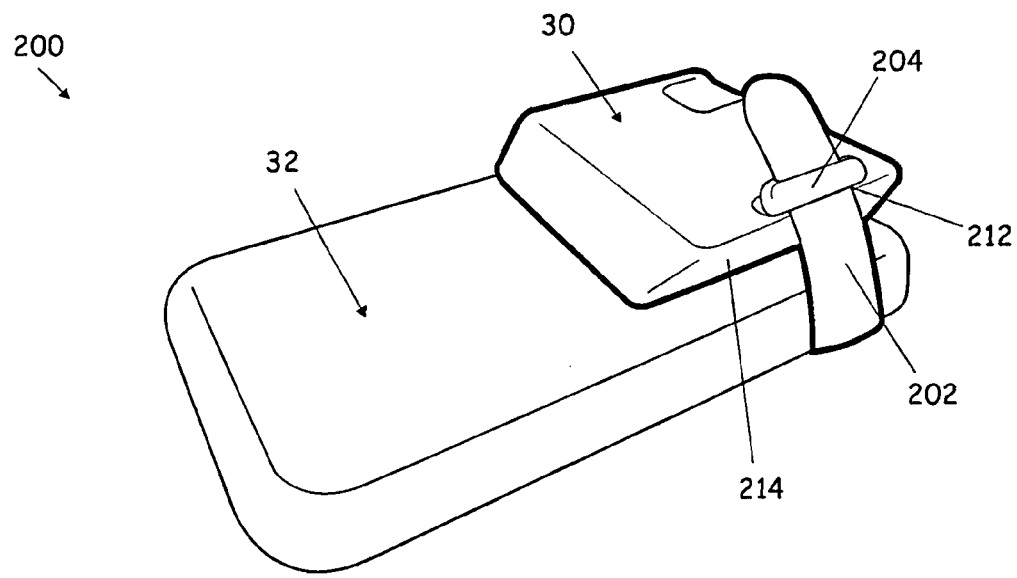
Figure 19:
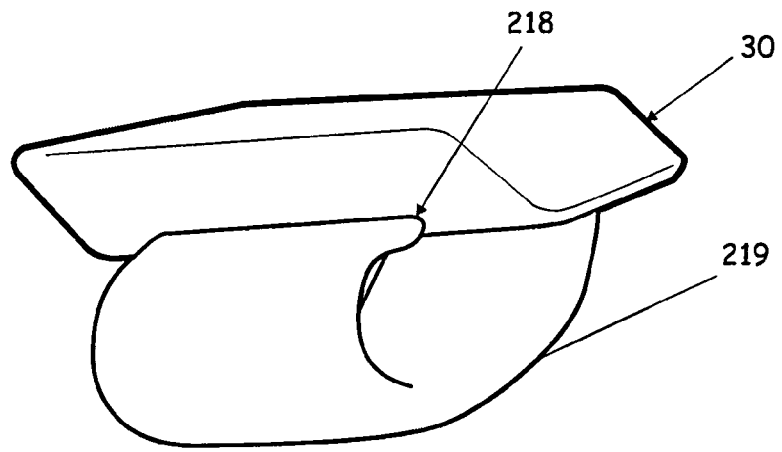
FIGS. 19 and 20 are perspective views of a cuff arrangement for mounting a light box accessory to a mobile device in an embodiment of the invention.
Figure 20:
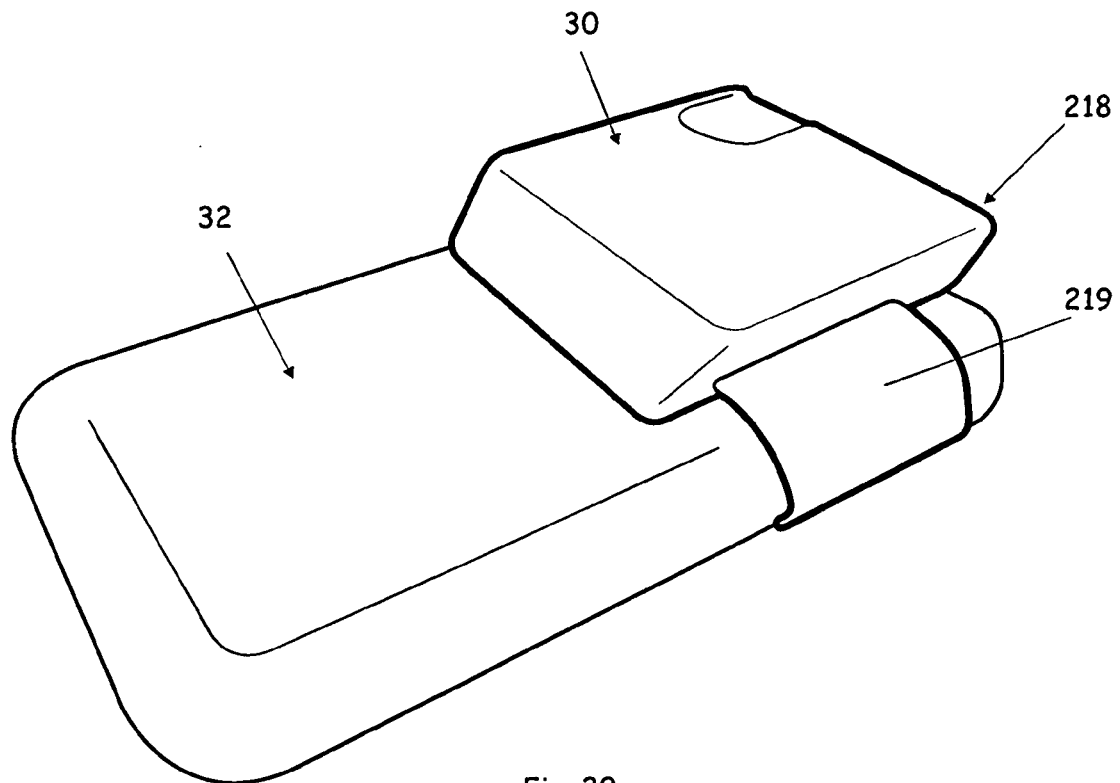

Referring to FIGS. 17 through 26, alternative means for selectively coupling the light box accessory 30 to the mobile device 32 that are alternatives to the magnetic coupling are depicted in embodiments of the invention. In one embodiment, an elastic binder arrangement 200 is implemented. An elastic strap 202 including an adjustable clasp 204 is affixed at one end 206 to a first lateral side 208 of the light box accessory 30 (FIG. 17). A slot 212 is formed an a second, opposing side 214 of the light box accessory 30. In operation, the light box accessory 30 is placed in an operative position on the camera face 62 of the mobile device 32. The elastic strap 202 is wrapped around the mobile device 32 coupled with the slot 212 so that the adjustable clasp 204 engages the slot 212 (FIG. 18). The adjustable clasp 204 can be adjusted so that the elastic strap 202 is in tension when the adjustable clasp 204 engages the slot 212.

In another embodiment, an expandable cuff arrangement 218 is implemented. An expandable cuff 219 is affixed to the light box accessory 30 (FIGS. 19 and 20) for sliding over the mobile device 32. The expandable cuff 219 is dimensioned to be put in tension when slid over the mobile device 32.

Figure 21:
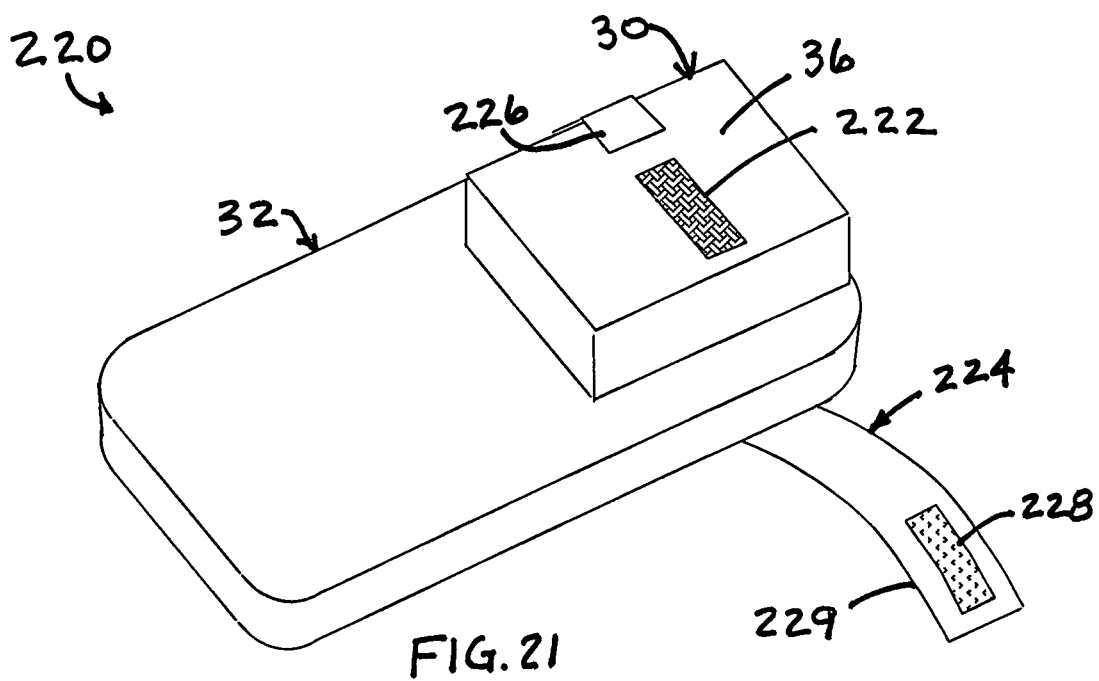
FIGS. 21 and 22 are perspective views of a hook-and-loop fabric arrangement for mounting a light box accessory to a mobile device in an embodiment of the invention.
Figure 22:
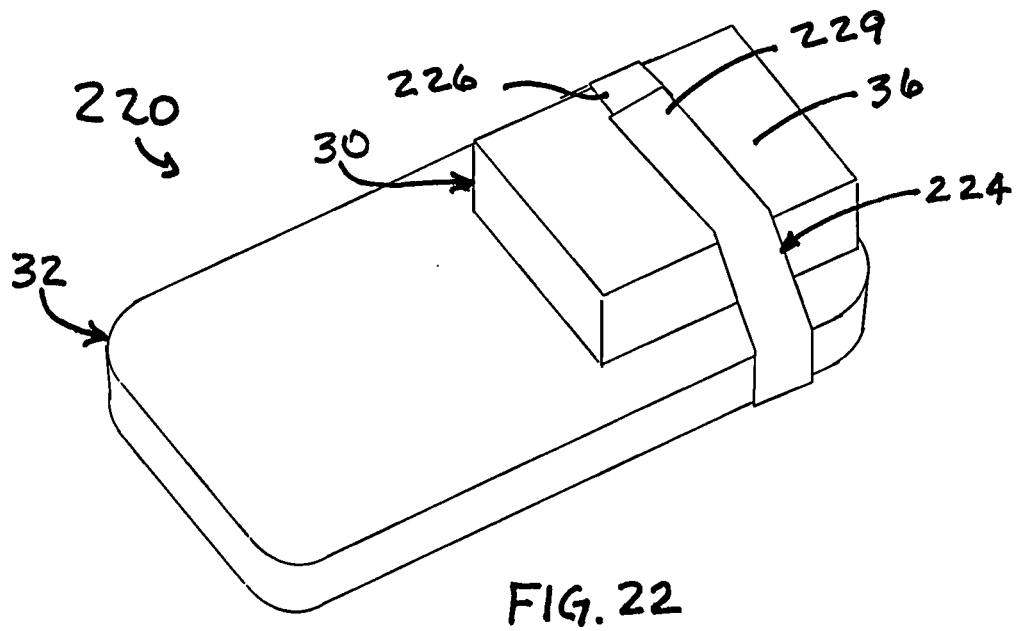

In another embodiment, a hook-and-loop fabric (e.g., VELCRO) fastening arrangement 220 is implemented (FIGS. 21 and 22). In this embodiment, a hook fabric 222 is affixed to the distal face 36 of the light box accessory 30. A strap 224, having one end 226 affixed to the light box accessory 30 and a loop fabric 228 affixed at an opposing end 229, is wrapped around the mobile device 32 so that the hook fabric 222 is engaged with the loop fabric 228.

In yet another embodiment, a slot-and-rail arrangement 230 is implemented (FIGS. 23 through 26). In this embodiment, the proximal face 196 of the light box accessory 30 includes structure that defines a keyway 232 having an open end 234 and a closed end 236 that lie along an axis 238. A rail 242 is affixed to the camera face 62 for engaging the keyway 232. The keyway 232 and rail 242 include complimentary cross-sections to enable capture of the rail 242 within the keyway 232 (e.g., T-slot or dovetail).

In one embodiment, affixing the rail 242 to the camera face 62 involves inserting the rail 242 into the keyway 232 so that a registration end 243 of the rail 242 registers against the closed end 236 of the keyway 232 as a temporary subassembly 244 (FIGS. 23 and 24) In this arrangement, the exposed face of the rail 242 is an engaging face 246 that engages the camera face 62. An adhesive can be applied to the engaging face 246 of the rail 242 in the temporary subassembly 244. Alternatively, the rail 242 can be prefabricated with a layer of adhesive on the engaging face 244, protected by a foil or paper covering; the covering is removed to expose the adhesive. The light box accessory 30 is then positioned over the camera face 62 of the mobile device so that the view port 64 of the light box accessory 30 is properly aligned with the camera 248 of the mobile device 32. The temporary subassembly 244 is then pressed against the camera face 62, so that the adhesive-coated engaging face 246 is affixed to the camera face 62. The light box accessory 30 is then removed from the rail 242 by sliding the light box accessory 30 so that the closed end 236 is lifted away from the rail 242.

Subsequently, the light box accessory 30 can be selectively coupled to the mobile device 32 by sliding the light box accessory 30 onto the rail 242 (FIGS. 25 and 26).

Functionally, the rail 242 aligns the light box accessory 30 for operation when the closed end 236 of the keyway 232 is engaged with the registration end 243 of the rail 242.

Figure 27:
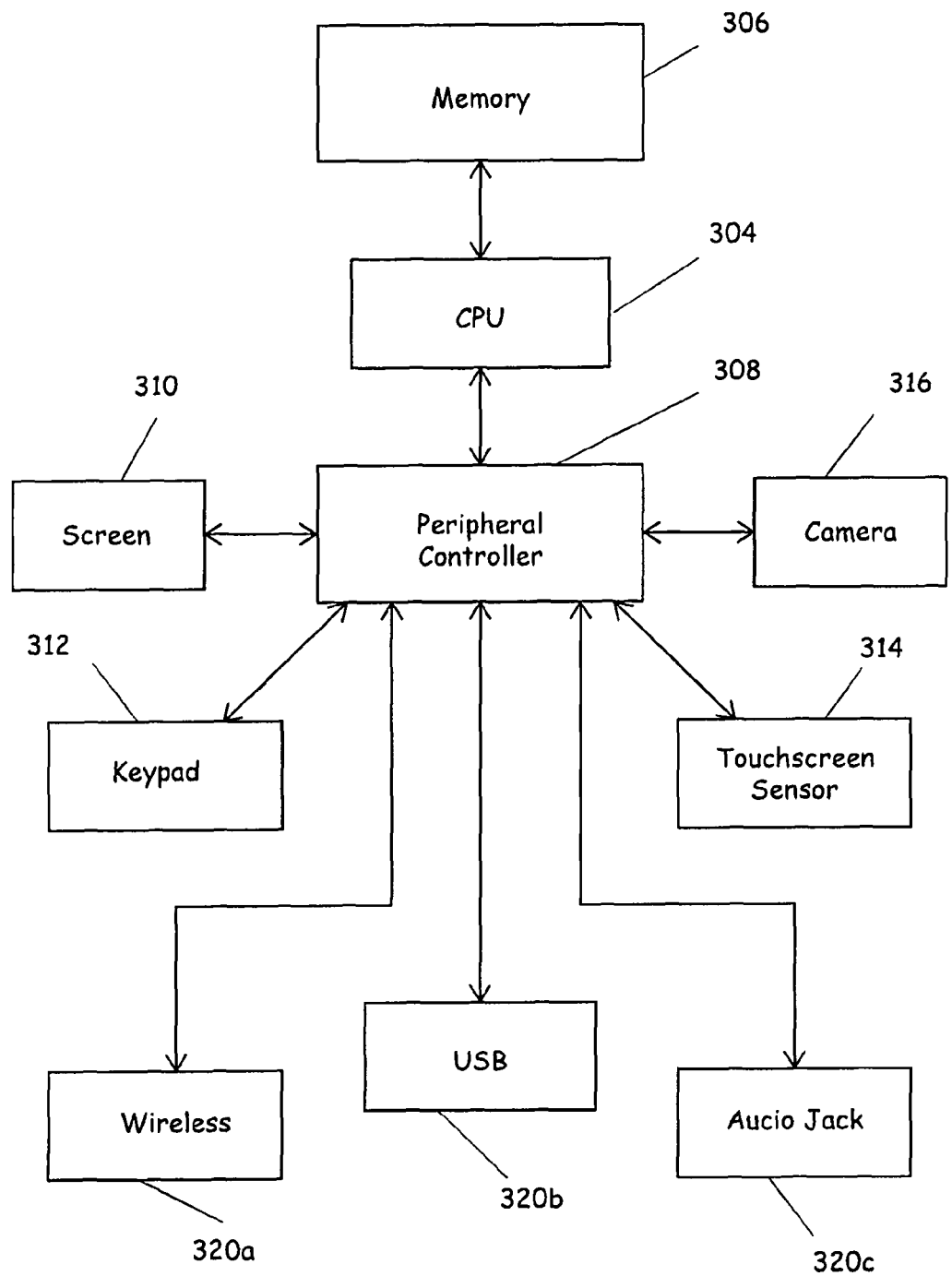
FIG. 27 is a schematic view of a mobile device used for the colorimetric test strip analysis and disease management platform in an embodiment of the invention.
Figure 28:
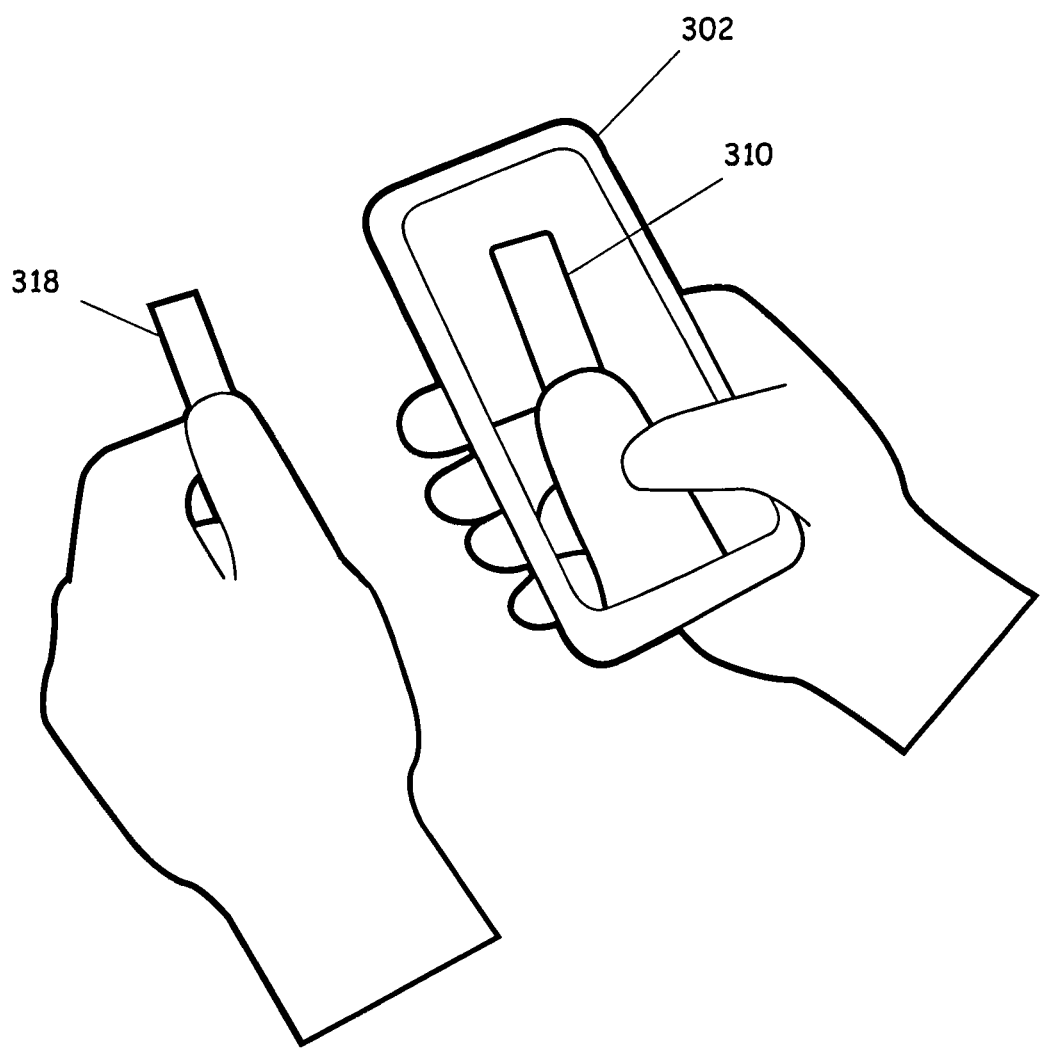
FIG. 28 is a perspective view of a mobile device in an embodiment of the invention as used to perform colorimetric test strip analysis with the patient holding the colorimetric test strip in front of the camera of the mobile device.
Figure 29:
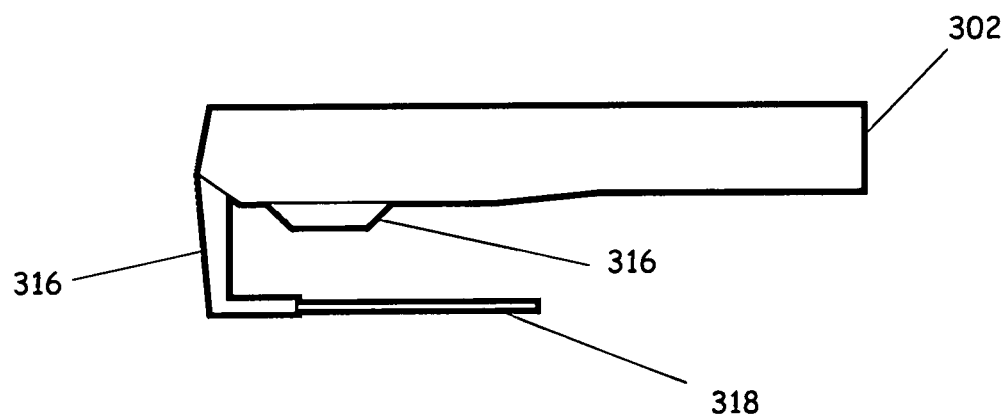
FIG. 29 is a side view of a mobile device in an embodiment of the invention as used to perform colorimetric test strip analysis with a clip-on casing holding the colorimetric test strip in front of the camera of the mobile device.

Referring to FIGS. 27 through 29, a mobile device 302 is depicted in alternative embodiments of the invention. The mobile device 302, such as a mobile phone with an integrated camera, can comprise a central processing unit (CPU) 304 that is connected to memory 306 and a peripheral controller 308. The peripheral controller 308 can interface with components that interact with the user and the physical world, such as a screen 310, a keypad 312, a touchscreen sensor 314 and a digital camera 316. The peripheral controller 308 can also be operatively coupled with general purpose communication interfaces 320 for communicating with external devices, including, but not limited to a wireless communication controller 320a, a USB port 320b and an audio jack 320c.

The colorimetric test strip analysis aspect is depicted in FIGS. 28 and 29. The digital camera 316 of the mobile device 302 is used to analyze the colorimetric test strip 318. In one embodiment, depicted in FIG. 28, the colorimetric test strip is held within close proximity of the camera of the mobile device 302 by the patient. In another embodiment, depicted in FIG. 29, the colorimetric test strip is held at a specific distance and position relative to the camera of the mobile device 302 by a clip-on casing 322 that attaches to the phone.

Figure 30:
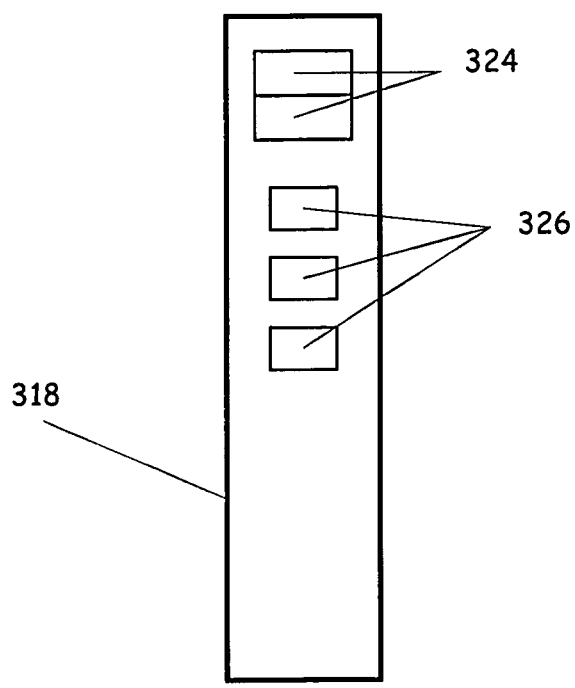
FIG. 30 is a plan view of an example colorimetric test strip in an embodiment of the invention.
Figure 31:
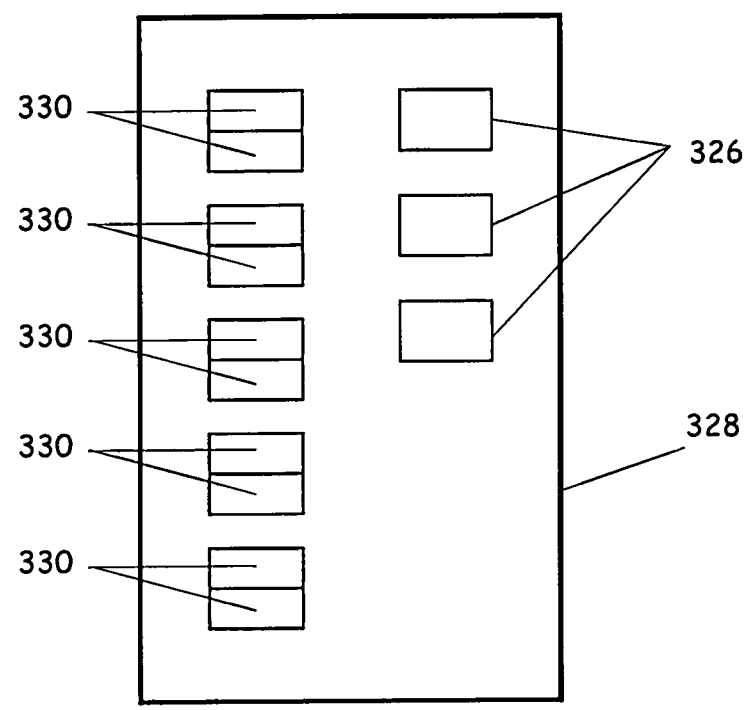
FIG. 31 is a plan view of an example reference color chart in an embodiment of the invention.

Referring to FIG. 30, a colorimetric test strip 318 is depicted in an embodiment of the invention. It comprises one or several reagent areas 324 that change color when they come in contact with a certain bodily fluid that is being tested, such as blood or saliva. The colorimetric test strip 318 also comprises of one or several in situ calibration color patches 326. These in situ calibration colors are identically reproduced on each colorimetric test strip 318 and also as initial calibration color patches 326' on a reference color chart 328 (FIG. 31). In some embodiments, one of the in situ calibration colors can be of a pure white color.

Referring to FIG. 31, a reference color chart 328 is depicted in an embodiment of the invention. The reference color chart 328 comprises one or several initial calibration color patches 326' as previously described, as well as reference color patches 330. Each of these reference colors corresponds to a test result reading that can be produced by the colorimetric test strip 318. A lighting condition equalization sequence can be employed to compensate for changes in lighting conditions between the detection of the reference color chart 328 and the detection of the colorimetric test strip 318.

Figure 32:
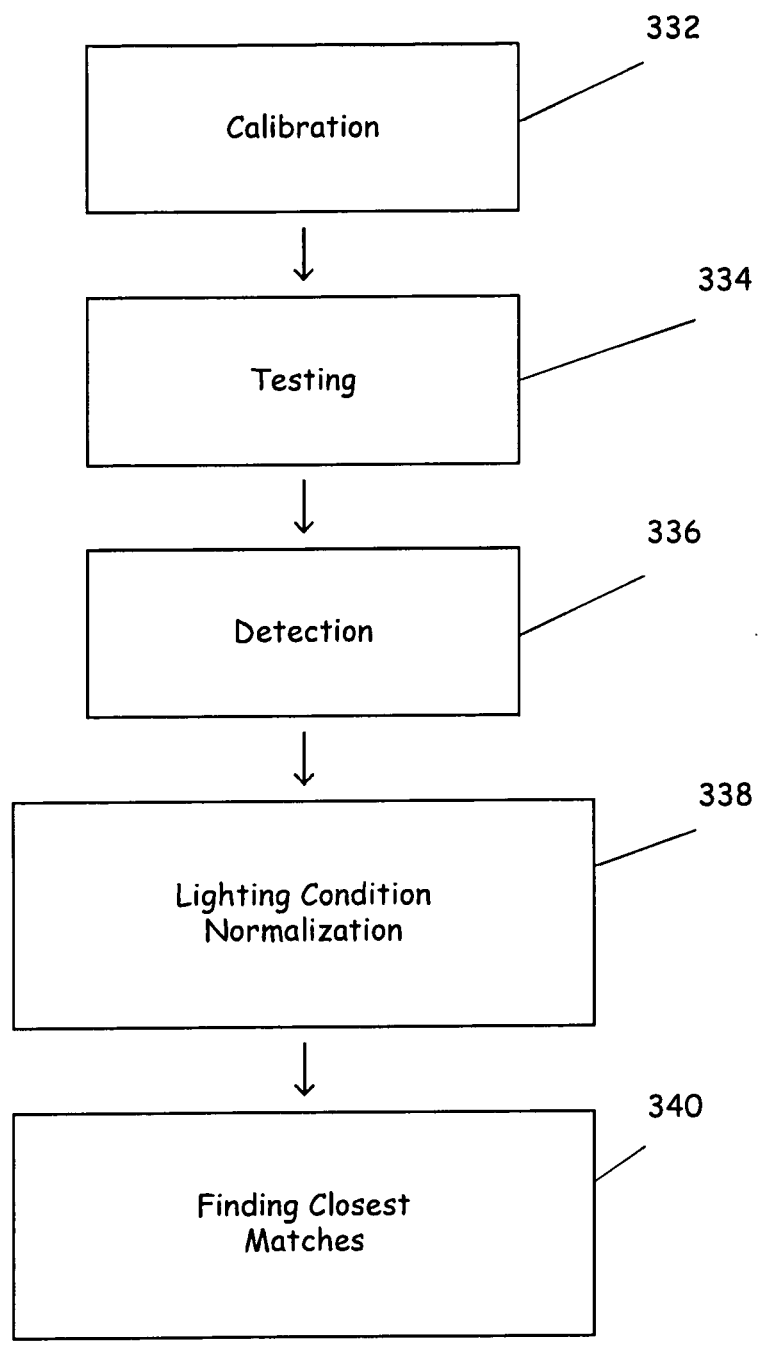
FIG. 32 is a flow chart of an embodiment of the invention.

Referring to FIG. 32, a general, overall process for colorimetric strip analysis is depicted in an embodiment of the invention. In this embodiment, step 332 is an initial calibration step, during which the patient uses the digital camera 316 of the mobile device 302 to acquire a digital image of the reference color chart 328. The digital camera 316 thereby detects color values for both the calibration color patches 326' and the reference color patches 330 contained in the reference color chart 328. The mobile device 302 can be configured to detect these color values automatically by finding the various color patches 326', 330 in the digital image and analyzing the colors of the patches. Location of the color patches 326' and/or color patches 330 can be performed using methods such as disclosed in references [3] through [6] listed in the "References" section herein, the disclosures of which are hereby incorporated by reference herein in their entirety except for express definitions therein. A single color value can be computed for a given detected color patch using median or mean statistics of the color values that are contained in its area. The color values are then stored in the memory 306 of the mobile device 302 for subsequent use.

Alternatively, images of standard colors can be entered into the mobile device by taking a sequence of images, each image including different reference colors. This approach is particularly suitable where the camera can only view targets of limited size, such as with the light box accessory 30.

Functionally, the color values acquired in the initial calibration step 332 serves to calibrate the digital camera 316 of the mobile device 302. The color values for both the initial calibration color patches 326' and the reference color patches 330 are known, and can be correlated with the respective color values by the software and stored in the memory 306 of the mobile device 302. The color values thus acquired provides an extensive calibration data base from which color values detected by the digital camera 316 can be interpreted against standardized colors. The initial calibration step 332 need only be performed once on a given mobile device 302, thereby taking into account the specific properties of the digital camera 316.

Step 334 is the testing step, during which the patient puts a small quantity of the bodily fluid being tested on the one or several reagent areas of the colorimetric test strip 318.

Step 336 is the colorimetric test strip detection step, during which the colorimetric test strip 318 is positioned in front of the camera 316 of the mobile device 302 as previously described and the colors of the reagent areas 324 and in situ calibration color patches 326 are detected by taking a photograph and finding the reagent areas and color patches in it automatically as described above. See References [3]-[6].

Step 338 is the application of the lighting condition equalization. This step is described in detail below.

Figure 33:
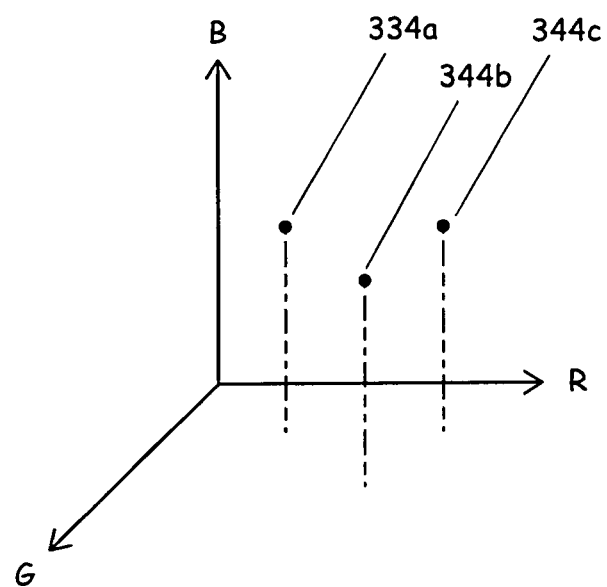
FIG. 33 is a graphical representation of the detected color values of a physical object of fixed color in different illumination conditions in an embodiment of the invention.

Step 340 is the computation of the test results from each reagent area 324 of the colorimetric strip 318, for example by finding the closest matches between the detected color of each reagent area 324 (after lighting condition equalization) and the set of reference colors from the reference color patches 330 stored in memory. These one or several test readings are then available to the patient and to the disease management system on the mobile device 302. This step is also described in more detail below. The problem that the lighting condition equalization sequence resolves is depicted in FIG. 33, which depicts in an arbitrary 3-dimensional standard red-green-blue color space (sRGB). For the purpose of this example, the different apparent color values 344a, 344b and 344c are that which a physical object of a fixed color can have in different lighting conditions. For example, a given color patch viewed in predominantly fluorescent light (344a) will generally reflect at a spectral intensity differently than one viewed in incandescent light (334b), which will reflect at a spectral intensity differently than one viewed in predominantly sunlight (344c). The equalization process takes into account such differing ambient lighting conditions.

Figure 34:
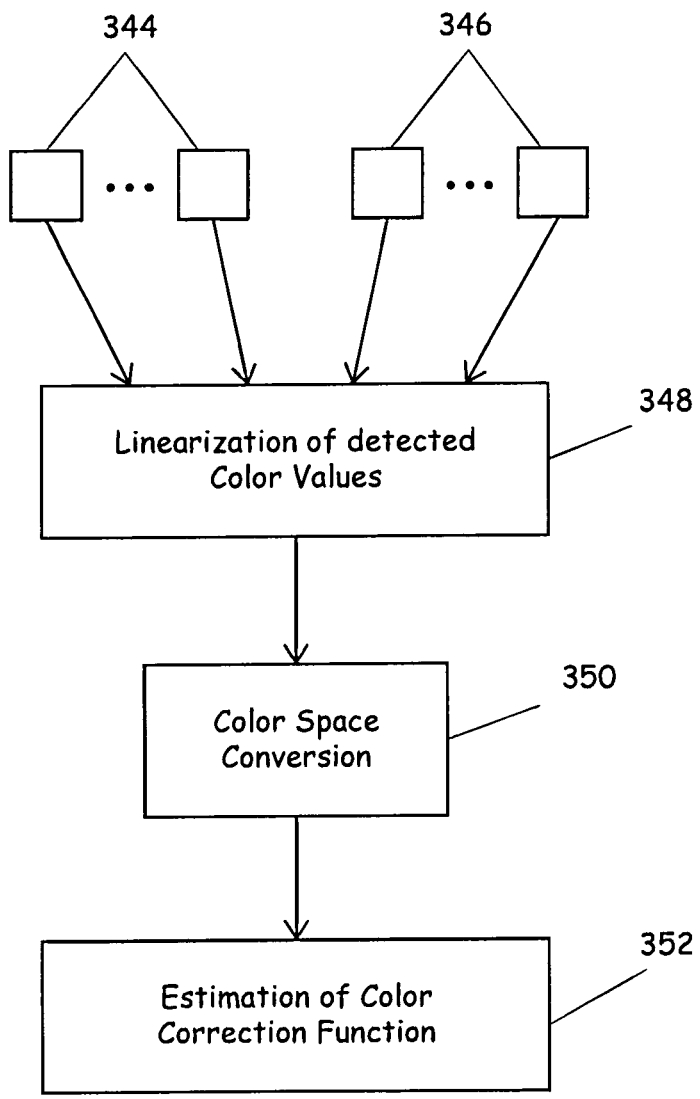
FIG. 34 is a flow chart of lighting condition equalization method used in an embodiment of the invention.

Referring to FIG. 34, a method for lighting condition equalization is depicted in an embodiment of the invention. The inputs are the detected color values 344 of the initial calibration color patches 326' on the reference chart 328 and the detected color values 346 of the in situ calibration color patches 326 on the colorimetric test strip 318. The step 348 is the linearization of these input-detected color values by applying an inverse Gamma correction function independently to each channel of each such color value to undo post-processing done automatically by the digital camera.

This inverse Gamma correction function is defined as follows in the commonly used sRGB color space:

$$I_{linear} = \begin{cases} \dfrac{I_{sRGB}}{12.92} & \text{if } I_{sRGB} \leq 0.04045 \\ \left(\dfrac{I_{sRGB} + 0.055}{1.055}\right)^{2.4}, & \text{otherwise} \end{cases} \quad \text{Eq. (1)}$$

where I represents a color intensity value in one color channel. In another embodiment, the following approximate inverse Gamma correction function can be used in most color spaces:

$$I_{linear} = (I_{non-linear})^{1/\gamma} \quad \text{Eq. (2)}$$

where $\gamma$ is an image format and camera dependent value and I represents a color intensity value in one color channel.

The step 350 is the optional step of converting the detected color values from the color space in which they were detected by the camera 316 of the mobile device 302 to any specific color space, including but not limited to sRGB, Commission Internationale de l'Eclairage (CIE) XYZ or CIELAB, in which the estimation of the color correction function step 352 will be performed. In some cases, this will not be necessary as the detected color values will already be in the appropriate color space.

The step 352 is the estimation of the color correction function to model or otherwise account for the changes in lighting conditions and/or camera response between the initial calibration (when the detected reference colors of the reference patches 330 are stored in the memory 316 of the mobile device 302) and colorimetric test strip analysis (when the detected color values of the reagent areas 354 on the colorimetric test strip are compared against the detected reference colors of the reference patches 330). In various embodiments, the color correction function $f(\ )$ transforms an input color vector $v_{in}$ to an output color vector $v_{out}$ in the same color space as follows:

$$v_{out} = f(v_{in}) \quad \text{Eq. (3)}$$

The color correction function $f(\ )$ can be estimated by minimizing an equation of the following form, sometimes referred to as a cost function:

$$\min \sum_k e(v_{c,k}, f(v_{a,k})) \quad \text{Eq. (4)}$$

where $e(\ )$ is an error function that quantifies the dissimilarity between the detected color $v_{c,k}$ of the $k^{th}$ calibration color patch on the reference chart 328 during the calibration phase and the detected color after color correction $f(v_{a,k})$ of the matching $k^{th}$ calibration color patch on the colorimetric test strip during the strip analysis phase. One example of such an error function is the sum-squared Euclidean distance, which when substituted into Eq. (4) leads to the following:

$$\min \sum_k \|v_{c,k} - f(v_{a,k})\|^2 \quad \text{Eq. (5)}$$

and reduces the problem of estimating the color correction function $f(\ )$ to a least squares estimation.

After color correction function $f(\ )$ is estimated, it can be applied to the detected color value $v_{RA}$ of each reagent area on the colorimetric test strip as follows:

$$\hat{v}_{RA} = f(v_{RA}) \quad \text{Eq. (6)}$$

The various embodiments below describe color correction functions for standard three-dimensional color spaces, such as the sRGB space, the CIE XYZ space and the CIE Lab space.

In one embodiment, a color correction function is defined as follows:

$$v_{out} = \begin{bmatrix} a_{11} & a_{12} & a_{13} \\ a_{21} & a_{22} & a_{23} \\ a_{31} & a_{32} & a_{33} \end{bmatrix} v_{in} \quad \text{Eq. (7)}$$

With a cost function defined as in Eq. (5), this embodiment requires at least three calibration color patches. The values $a_{ij}$ are estimated using an exact solution if exactly three calibration color patches are present and using linear least squares to obtain an approximate solution if there are more than three calibration color patches.

In a similar embodiment, the color correction function can be defined similarly but with a diagonal matrix:

$$v_{out} = \begin{bmatrix} a_{11} & 0 & 0 \\ 0 & a_{22} & 0 \\ 0 & 0 & a_{33} \end{bmatrix} v_{in} \quad \text{Eq. (8)}$$

With a cost function defined as in Eq. (5), this embodiment requires at least one calibration color patch. The values $a_{ij}$ are estimated using an exact solution if exactly one calibration color patch is present and using linear least squares to obtain an approximate solution if there is more than one calibration color patches.

In yet another embodiment, the color correction function is defined as follows:

$$v_{out} = \begin{bmatrix} a_{11} & a_{12} & a_{13} \\ a_{21} & a_{22} & a_{23} \\ a_{31} & a_{32} & a_{33} \end{bmatrix} v_{in} + \begin{bmatrix} b_1 \\ b_2 \\ b_3 \end{bmatrix} \quad \text{Eq. (9)}$$

With a cost function defined as in Eq. (5), this embodiment requires at least four calibration color patches. The values $a_{ij}$ and $b_i$ are estimated using an exact solution if exactly four calibration color patches are present and using linear least squares to obtain an approximate solution if there are more than four calibration color patches.

In another embodiment, the color correction function is defined with a diagonal matrix:

$$v_{out} = \begin{bmatrix} a_{11} & 0 & 0 \\ 0 & a_{22} & 0 \\ 0 & 0 & a_{33} \end{bmatrix} v_{in} + \begin{bmatrix} b_1 \\ b_2 \\ b_3 \end{bmatrix} \quad \text{Eq. (10)}$$

With a cost function defined as in Eq. (5), this embodiment requires at least two calibration color patches. The values $a_{ij}$ and $b_i$ are estimated using an exact solution if exactly two calibration color patches are present and using linear least squares to obtain an approximate solution if there are more than two calibration color patches.

In another embodiment, the color correction function is defined as follows:

$$v_{out} = \begin{bmatrix} c_{11} & 0 & 0 \\ 0 & c_{22} & 0 \\ 0 & 0 & c_{33} \end{bmatrix} \begin{bmatrix} v_{in,1}^2 \\ v_{in,2}^2 \\ v_{in,3}^2 \end{bmatrix} + \begin{bmatrix} a_{11} & 0 & 0 \\ 0 & a_{22} & 0 \\ 0 & 0 & a_{33} \end{bmatrix} v_{in} + \begin{bmatrix} b_1 \\ b_2 \\ b_3 \end{bmatrix} \quad \text{Eq. (11)}$$

With a cost function defined as in Eq. (5), this embodiment requires at least three calibration color patches. The values $a_{ij}$ and $b_i$ and $c_{ij}$ are estimated using an exact solution if exactly three calibration color patches are present and using linear least squares to obtain an approximate solution if there are more than three calibration color patches.

The disclosed embodiments have varying requirements in terms of the necessary number of different calibration color patches. In the situation where a single calibration color patch is used, this patch can comprise colors that reflect in the red, green and blue wavelengths (e.g., gray or white). In the situation when several calibration color patches are used, they can be tailored to reflect substantially in wavelengths that are as distinct as possible from each other (e.g., red, green and blue wavelengths respectively if there are three such patches), in order to cover a wide spectrum of colors. Another approach is to choose these calibration colors only from the color spectrum spanned by the reference color patches 330, which may improve performance in that specific color range. Still another consideration is to choose colors that are particularly sensitive to commonly encountered lighting conditions (e.g., wavelengths that experience the greatest reflective changes between, for example, sunlight or incandescent light and fluorescent light).

Figure 35:
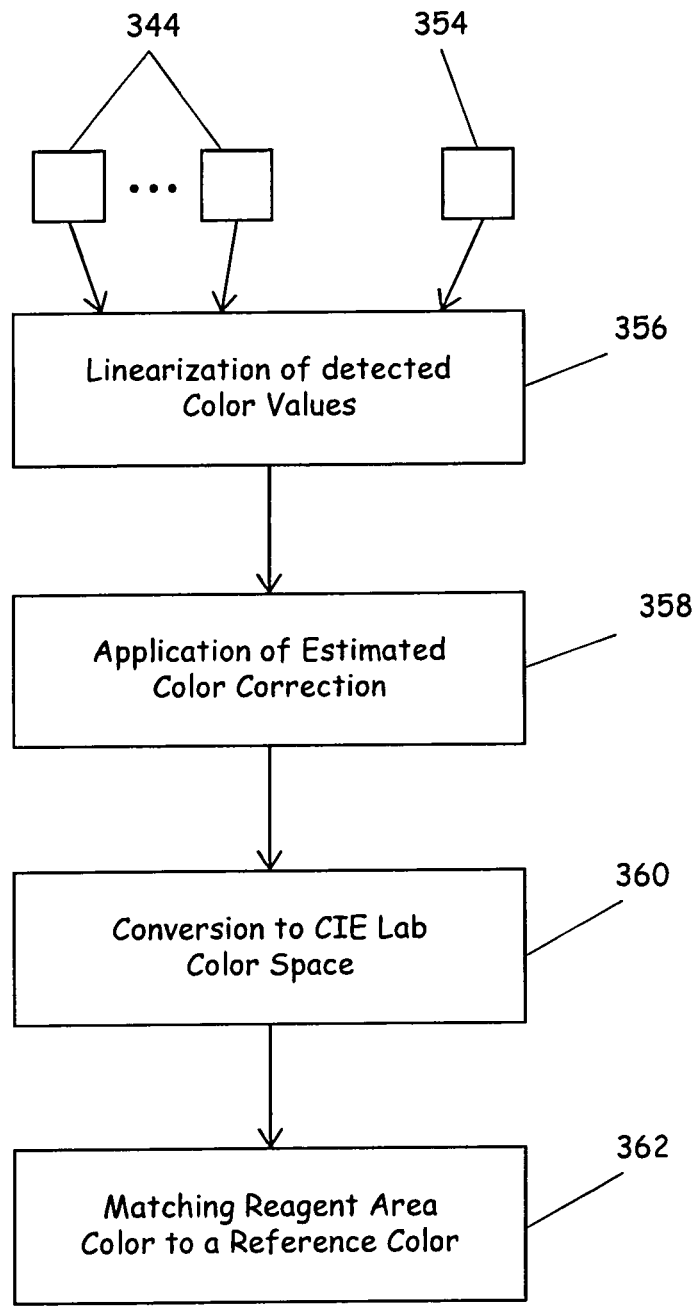
FIG. 35 is a flow chart depicting the process of finding the closest matching reference color for each reagent area on the colorimetric strip in an embodiment of the invention.

The process at step 340 of finding the closest match for each reagent area of the colorimetric test strip is depicted in more detail in FIG. 35. The inputs for step 340 are the detected color values of the reference color patches 330 on the reference color chart 328 and the detected color value 354 of the reagent area 324 in question on the colorimetric test strip 318.

The step 356 is the linearization of these input detected color values by applying to each the inverse Gamma correction function of Eq. (1) or Eq. (2), the same as performed at step 348 of FIG. 34. With certain mobile devices, the linearization step 356 can be considered optional (e.g., for systems that provide access to raw image data instead of just conditioned image data).

The step 358 is the application of the color correction function estimated in step 352 above to the linearized detected color value of the reagent area 324 in question using Eq. (6). If the color correction estimation was done in a color space different from the one the color was detected in, this step also can include an appropriate color space conversion before the application of the color correction function.

The step 360 is the conversion of the linearized and lighting equalized color values of the reagent area 324 in question and the detected linearized color values of the in situ calibration color patches 326 on the colorimetric strip 318 to a color space that is appropriate for color matching, such as the CIELAB color spaces that model human perception. For conversion to the CIELAB color space, it may be necessary to first convert the color values to the CIE XYZ color space, which can be accomplished by a matrix multiplication for most standard color spaces, such as the sRGB color space:

$$\begin{bmatrix} X \\ Y \\ Z \end{bmatrix} = [M] \begin{bmatrix} R \\ G \\ B \end{bmatrix} \quad \text{Eq. (12)}$$

where M is the appropriate 3×3 conversion matrix. The conversion to the CIELAB color space can then be accomplished according to the following equations, found in reference [7], which is incorporated by reference herein except for express definitions contained therein:

$$L^* = 116 f(Y/Y_n) - 16$$

$$a^* = 500[f(X/X_n) - f(Y/Y_n)]$$

$$b^* = 200[f(Y/Y_n) - f(Z/Z_n)] \quad \text{Eq. (13)}$$

where $$f(t) = \begin{cases} t^{1/3} & \text{if } t > \left(\frac{6}{29}\right)^3 \\ \frac{1}{3}\left(\frac{29}{6}\right)^2 t + \frac{4}{29} & \text{otherwise} \end{cases} \quad \text{Eq. (14)}$$

and $\{X_N, Y_N, Z_N\}$ are the CIE XYZ color values of the pure white calibration patch.

In one embodiment, after linearization, lighting equalization and conversion to the CIELAB color space, a step 362 comprises matching the detected, linearized and lighting equalized CIELAB color value of the reagent area in question to the reference color patch 330 that has the closest linearized detected CIELAB color value according to the following equation:

$$\operatorname*{argmin}_{i} \|\hat{v}_{RA} - v_i\| \quad \text{Eq. (15)}$$

where $\hat{v}_{RA}$ is the lighting equalized CIELAB color value of the reagent area in question, $v_i$ is the linearized CIELAB color value of the $i^{th}$ reference color patch and argmin signifies that evaluating Eq. (15) results in the argument that minimizes the expression, in this case the reference color patch index i, instead of the minimum value of the expression. Once this match is established the test reading of the reagent area in question can be established as $r_{RA} = r_i$, with $r_i$ being the test reading of the matched reference color patch as obtained in Eq. (15). The reagent area test reading is then available to the patient and to the disease management system on the mobile device.

In another embodiment, when the test readings associated with each reference color patch are numerical values, the reading value of the reagent area in question can be computed as a weighted average of the test reading values associated with the reference color patches that are in the set $\mathcal{N}$. This set is composed of the reference color patches that have a CIELAB color value that is one of the N closest such values to the lighting equalized CIELAB color value of the reagent area in question. The weighted average is defined as follows:

$$r_{RA} = \sum_{i \in N} w_i r_i \qquad \text{Eq. (16)}$$

where $r_{RA}$ is the test reading value assigned to the reagent area in question, $r_i$ is the test reading value that corresponds to the $i^{th}$ reference color patch and the weights $w_i$ are proportional to a measure of closeness of the CIELAB color value of the $i^{th}$ reference color patch and the lighting equalized CIELAB color value of the reagent area in question:

$$w_i = \frac{sim(\hat{v}_{RA}, v_i)}{\sum_{i \in N} sim(\hat{v}_{RA}, v_i)} \qquad \text{Eq. (17)}$$

where $\hat{v}_{RA}$ and $v_i$ are defined as above, and sim( ) is the measure of similarity that can be defined as the inverse of the Euclidean distance between the two color values:

$$sim(\hat{v}_{RA}, v_i) = \frac{1}{\|\hat{v}_{RA} - v_i\|} \qquad \text{Eq. (18)}$$

It is understood that the specific color spaces, such as CIELAB, used in some of the descriptions above are intended as examples and are non-limiting. It is axiomatic that other suitable color spaces, including but not limited to sRGB, CIE XYZ and CIELUV, may be used as well.

The process of finding the various color patches and reagent areas in the photographs captured by the camera of the mobile device can employ edge detection and shape recognition techniques, such as described in references [3] through [6] below, which are incorporated by reference above.

Figure 36:
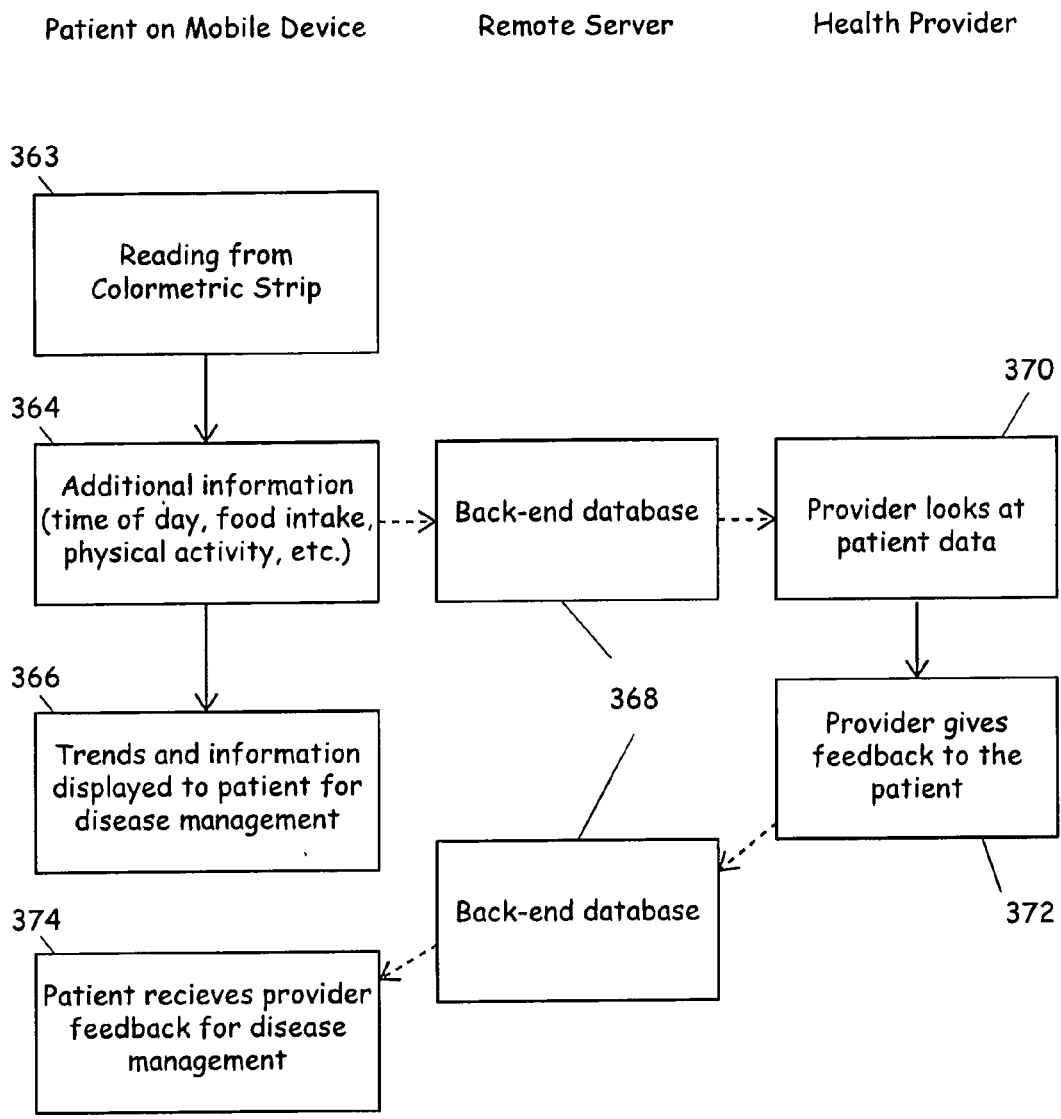
FIG. 36 is a flow chart of the disease management platform in an embodiment of the invention.

The disease management platform where the test readings collected using the above described colorimetric test strip analysis are used is depicted in FIG. 36. It comprises three components: a software application on the mobile device 302 of the patient, a remote server and a software application on the device of a health provider. The platform functions as follows: The patient starts by collecting test readings 363 using one or several colorimetric test strips 318 using a mobile device 302 as previously described. The patient then enters additional information 364 such as time of day, food intake and physical activity using the software on the mobile device 302. This and previously entered information can be aggregated and analyzed on the mobile device to produce reports and FIG. 366 that are displayed to the patient for disease management. In addition, the data can be transferred to a database 368 on the remote server. This allows the data to be accessed 370 by a health provider in a software application. The health provider then analyzes the data and has the option to send feedback 372, such as medication dosage or lifestyle adjustments, to the patient. This feedback can be sent to the database 368 on the remote server where it can be stored and sent to the mobile device of the patient, which displays the received feedback 374.

Figure 37:
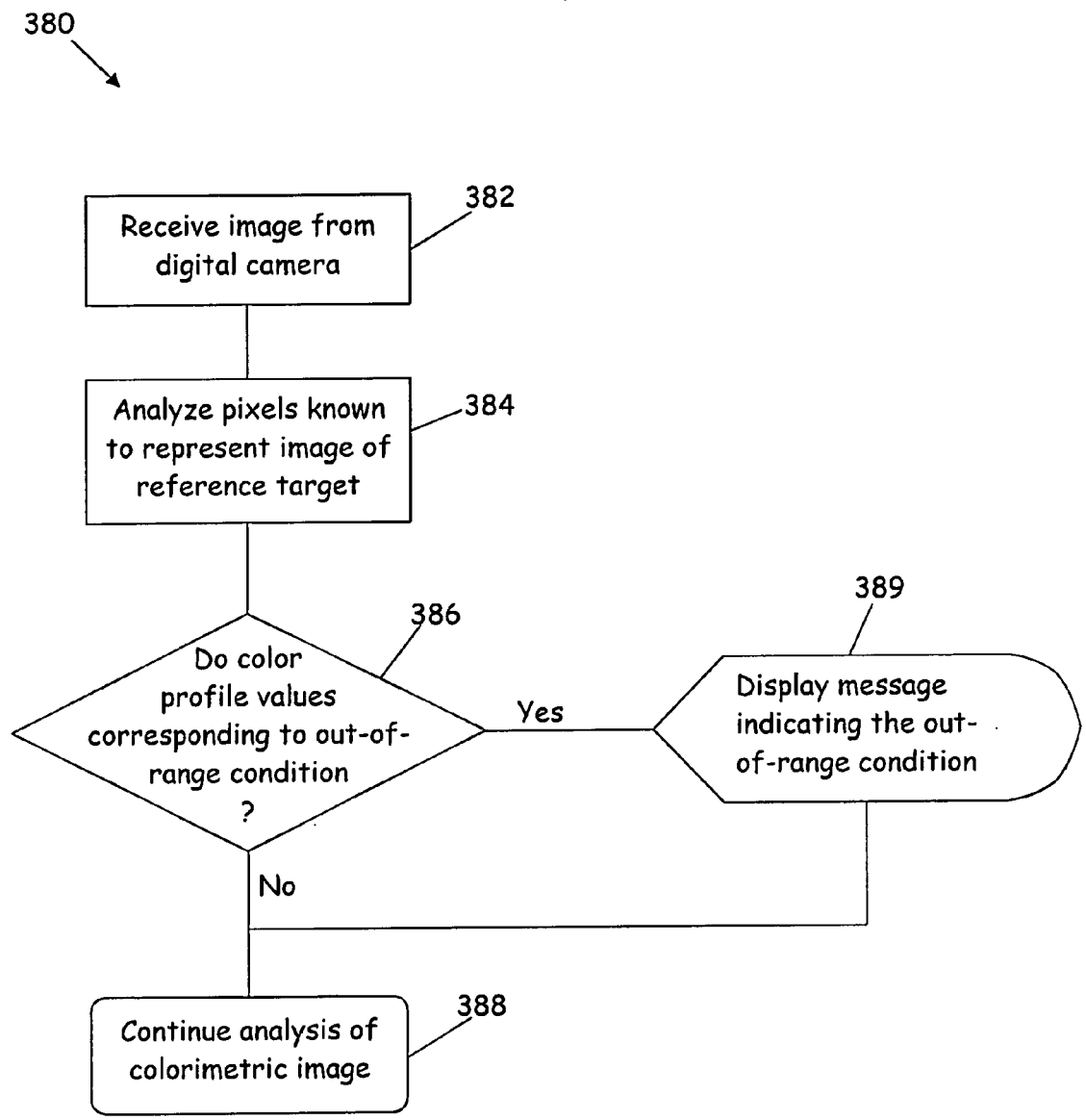
FIG. 37 is a flow chart of a sequence for determining that an out-of-range event has occurred in an embodiment of the invention.

Referring to FIG. 37, a sequence 380 for determining that an out-of-range event has occurred is depicted in an embodiment of the invention. First, image data is received from the digital camera (step 382) and pixels known to represent the image of the in situ calibration target analyzed (step 384) using methods described herein. The analyzed pixels are then compared against color profile values that correspond to an out-of-range condition (step 386). If the color profile does not correspond to the out of range condition, the remainder of the analysis procedure is executed (step 388). If the color profile is within a range of values that corresponds to an out-of-range condition (i.e., is indicative that the colored light source is for the given out-of-range condition is illuminating the in situ calibration target 102), a message is displayed to inform the user that the out-of-range condition is indicated (step 389). In the depicted embodiment, the routine continues with analysis of the colorimetric image (step 388). Alternatively, the procedure can branch to one of a variety of subroutines, including termination, waiting for further instruction, or advising regarding remedial measures.

It is noted that the same general method can be utilized for a plurality of out-of-range conditions if a different colored light is utilized for each out-of-range condition. That is, substantially different colored lights will cause a different irregular color profile.

The various steps, processes and sequences described above can be provided as instructions or algorithms on a tangible medium, for example in the memory 306 for reading and execution by the CPU 304. The various steps of FIG. 32 and FIGS. 34 through 37 are shown and discussed in sequences that are representative of particular embodiments of the invention. It is understood that certain embodiments can employ only some of the steps disclosed herein, and that the steps can, in some instances, be performed in a different sequence.

It is noted that U.S. Patent Application Publication No. 2008/0025599 to Cho et al. (Cho) discloses a method for matching colors detected by the camera of a mobile device to reference colors stored in its memory from a previous detection. These reference colors are also detected using a colorimeter to record their true color values and to assign one of the true color values to the new color being matched. Cho does not disclose lighting condition equalization; instead, Cho only describes the matching process and thus assuming constant ambient lighting conditions.

U.S. Pat. No. 6,628,829 to Chasen (Chasen) is directed to paint color matching and discloses a method for matching colors stored in the memory of a device to a surface color. The device of Chasen requires a test card with certain calibration colors to enable the estimation of the change in the lighting conditions between the detection of the reference colors stored in memory and the detection of the surface color to be analyzed. Chasen does not disclose color correction functions or describe the details of the any matching process.

Dell et al. [1] (Dell) describes a mobile phone based system for automated immunoassay analysis. The Dell disclosure makes use of a one-dimensional color space that consists of the color intensity. Likewise, Wang et al. [2] (Wang) describe a method for mobile phone camera based analysis of a microchip assay for diagnosis of ovarian cancer. The Wang disclosure makes use of a one-dimensional color intensity space as well. Both applications discussed by Dell and Wang do not require the knowledge of the full color.

Color correction methods have also been widely used in the context of camera calibration. U.S. Pat. No. 7,414,758 to Vaughn (Vaughn) and U.S. Patent Application Publication No. US 2007/0177032 to Wong (Wong) disclose methods for calibrating a digital image sensor by acquiring a photograph of a test card with patches of known colors. These known colors are then used to estimate parameters such as exposure, white balance correction, gamma correction, non-linearity compensation and color correction. Neither Vaughn nor Wong disclose any color matching aspect after the calibration is performed.

Methods for disease management for diabetes patients using mobile devices are disclosed in U.S. Patent Application Publication No. 2010/0145733 to Drucker et al. The invention describes software that runs on a mobile device to which an external blood glucose meter is connected in order to supply blood glucose measurements. Additional lifestyle information is entered directly on the mobile device. The collection and transfer of this information allows for analyzing the data to produce feedback for the patient, such as longitudinal trends and disease management advice. Embodiments of the invention of the instant does not require an external meter in addition to the mobile device to make the measurement, instead using the built-in camera of the mobile device for this task.

U.S. Pat. No. 8,145,431 to Kloepfer et al. ("Kloepfer") discloses an analyte testing device for use with a mobile processing device such as a mobile phone. Kloepfer discloses the use of a casing that attaches to the mobile phone and a lighting source contained within the casing. However, the lighting is directed for transmission through the test strip (backlighting), which adds to complexity of the optical system and cost of optical layout. Furthermore, the device of Kloepfer is configured to accept a wand that holds the test strip, the wand being of substantially greater cross-sectional dimension than the test strip. Accommodation of the backlighting optics and the wand dimensions combine for a bulky package that substantially increases the profile of the mobile phone.

Mudanyali et al., "Integrated Rapid-Diagnostic-Test Reader on a Cellphone," DOI:10.1039/C2LC40235A, (Apr. 16, 2012), discloses a cellphone based reader platform for various lateral flow immunochromatographic assays to sense the presence of a target analyte in a sample. Lighting control optics are mounted within an enclosure that is on a frame, the frame being adapted to slip over the camera end of the cellphone. The lighting control optics accommodate either transmission (backlighting) or reflection (frontal illumination) of the test strip. The lighting and optical system substantially add to the profile of the cellphone when coupled thereto. Also, cellphones of differing size and optical layout require different frames, as the frame is what provides alignment with the camera of the cellphone. Moreover, the platform must be totally removed to operate the camera of the mobile device for other purposes.

The following references, discussed above, are hereby incorporated by reference herein in their entirety except for express definitions or claims contained therein: U.S. Pat. No. 8,145,431 to Kloepfer et al.; U.S. Patent Application Publication No. 2011/0038765 to Drucker et al.; Mudanyali, et al., "Integrated Rapid-Diagnostic-Test Reader on a Cellphone," DOI:10.1039/C2LC40235A, (Apr. 16, 2012) (available at http://pubs.rsc.org, last visited Apr. 19, 2012); Lee, et al., "A simple and smart telemedicine device for developing regions: a pocket-sized colorimetric reader," Lab Chip, 2011, 11, 120, pp. 120-126 (Nov. 26, 2010) (available at http://pubs.rsc.org, last visited May 16, 2012); Dell, et al., "Towards a Point-of-Care Diagnostic System: Automated Analysis of Immunoassay Test Data on a Cell Phone," NSDR '11 (Jun. 28, 2011); "100 ppm/° C., 50 µA in SOT23-3 CMOS Voltage Reference," available at http://www.ti.com/lit/ds/symlink/ref2912.pdf (last visited Mar. 5, 2013); "LPV7215 580 nA Rail-to-Rail Input and Output, 1.8V, Push-Pull Output Comparator," available at http://html.alldatasheet.com/html-pdf/115571/NSC/LPV7215MF/56/1/LPV7215MF.html (last visited Mar. 3, 2013); "Low-Power Linear Active Thermistor™ ICs," available at http://ww1.microchip.com/downloads/en/DeviceDoc/21942e.pdf (last visited Mar. 3, 2013).

REFERENCES

[1] Nicola Dell et al., *Towards a Point-of-Care Diagnostic System: Automated Analysis of Immunoassay Test Data on a Cell Phone*. 5th ACM Workshop on Networked Systems for Developing Regions (NSDR), 2011.

[2] S. Wang et al., *Integration of cell phone imaging with microchip ELISA to detect ovarian cancer HE4 biomarker in urine at the point-of-care*. Lab on a Chip, 11(20), pp. 3411-3418, 2011.

[3] J. Canny, *A Computational Approach To Edge Detection*, IEEE Trans. Pattern Analysis and Machine Intelligence, 8(6), pp. 679-698, 1986.

[4] R. O. Duda and P. E. Hart, *Use of the Hough Transformation to Detect Lines and Curves in Pictures*. Comm. ACM, Vol. 15, pp. 11-15 (January, 1972).

[5] D. H. Ballard, *Generalizing the Hough Transform to Detect Arbitrary Shapes*, Pattern Recognition, Vol. 13, No. 2, p. 111-122, 1981.

[6] Claudio Rosito Jung and Rodrigo Schramm. 2004. *Rectangle Detection based on a Windowed Hough Transform*. In Proceedings of the Computer Graphics and Image Processing, XVII Brazilian Symposium (SIBGRAPI '04). IEEE Computer Society, Washington, D.C., USA, 113-120.

[7] Richard Szeliski, *Computer Vision: Algorithms and Applications*. Springer, 2010, pp. 80-84 (Section 2.3.2).

What is claimed is:

1. A light box accessory for analyzing colorimetric strips with a mobile device, said mobile device including a central processing unit and a digital camera, the accessory comprising:

an enclosure including a proximal cover, a perimeter wall and a distal cover, the proximal cover presenting a proximal face and including structure defining a view port that passes through said proximal cover, the distal cover presenting a distal face;

an aperture structure that defines an aperture within said enclosure, said aperture defining a viewing axis that is concentric therewith, said viewing axis being substantially normal to said aperture, said view port of said proximal cover being substantially concentric about said viewing axis;

structure defining a first slot for insertion of a colorimetric strip and a second slot arranged proximate an abutting end of said first slot, said first slot being configured for orienting said colorimetric strip to intersect said viewing axis, and said second slot being configured for verifying insertion of said colorimetric strip into said first slot;

an in situ calibration target disposed within said aperture structure of said light box accessory, said in situ calibration target having predetermined color characteristics;

at least one light source disposed within said enclosure, said at least one light source being arranged for illumination of said colorimetric test strip when said colorimetric test strip is registered within said slot;

a power source disposed within said enclosure and operatively coupled with said at least one light source; and a switch operatively coupled between said power source and said at least one light source for selective activation of said at least one light source, wherein said accessory is configured to communicate with said central processing unit of said mobile device only through said digital camera of said mobile device.

2. The light box accessory of claim 1, wherein said aperture structure is integrally formed with at least one of said perimeter wall and said distal cover.

3. The light box accessory of claim 1, wherein said switch is accessible on the exterior of the enclosure for manual energization of said at least one light source.

4. The light box accessory of claim 1, wherein said at least one light source is a light-emitting diode.

5. The light box accessory of claim 1, wherein said power source is at least one battery.

6. The light box accessory of claim 1, further comprising a macro lens disposed within the enclosure, the macro lens being substantially concentric about the viewing axis and being located between said view port and said in situ calibration target.

7. The light box accessory of claim 1, further comprising a circuit for detection of an out-of-range condition, said circuit including a colored light source arranged to illuminate said in situ calibration target when activated.

8. The light box accessory of claim 7, wherein said said circuit is one of a low battery detection circuit and a temperature out-of-range circuit.

9. The light box accessory of claim 1, further comprising a first circuit and a second circuit, each of the first and second circuits being for detection of out-of-range conditions, each of the first and second circuits including a respective colored light source, each of the respective colored light sources being arranged to illuminate said in situ calibration target when activated.

10. The light box accessory of claim 9, wherein:
said first circuit is configured to detect a first out-of-range condition;
said second circuit is configured to detect a second out-of-range condition;
said first out-of-range condition differs from said second out-of-range condition; and
a color of said respective colored light source of said first circuit differs from a color of said respective colored light source of said second circuit.

11. A method for colorimetric analysis of colorimetric test strips that implements a color correction, the method comprising:
providing a mobile device that includes a digital camera and a central processing unit (CPU), said CPU being operatively coupled to a storage medium and configured to receive instructions from said storage medium;
configuring said storage medium to include instructions readable by said CPU, said instructions including:
capturing at least one image of a plurality of standard colors with said digital camera;
converting said at least one image of said plurality of standard colors to a plurality of initial calibration color values;
providing a colorimetric strip exposed to a test fluid, said colorimetric strip including a reactive area;
providing an in situ calibration target disposed within an aperture structure of said light box accessory that includes at least one in situ calibration color thereon, said at least one in situ calibration color being unaffected by the presence of said test fluid, each of said at least one in situ calibration colors being substantially identical to a respective one of said plurality of standard colors;
obtaining a digital test image that includes both an image of said reactive area of said colorimetric strip and an image of said in situ calibration target;
analyzing portions of said digital test image known to represent said in situ calibration target to obtain a plurality of corresponding in situ quantitative color values;
comparing said corresponding quantitative color values with said initial calibration color values;
establishing a color correction function based on said corresponding in situ quantitative color values;
analyzing portions of said digital test image known to represent said reactive areas of said colorimetric strip to obtain a plurality of test color values corresponding to said reactive areas; and
applying said color correction function to said plurality of test color values; and
converting said plurality of test color values to at least one test reading.

12. The method of claim 11, wherein said plurality of standard colors are reference colors.

13. The method of claim 11 wherein said at least one image of a plurality of standard colors includes both calibration colors and reference colors.

14. The method of claim 11, further comprising linearizing said initial calibration color values and said in situ quantitative color values.

15. The method of claim 11, further comprising storing said plurality of initial calibration color values to said storage medium.

16. The method of claim 15, further comprising recalling said plurality of initial calibration color values from said storage medium before the step of comparing.

* * * * *